(12) United States Patent
Napoles et al.

(10) Patent No.: US 12,156,716 B1
(45) Date of Patent: Dec. 3, 2024

(54) RADIO FREQUENCY BIOSENSOR WITH INTEGRATED COMPENSATION

(71) Applicant: AMAZON TECHNOLOGIES, INC., Seattle, WA (US)

(72) Inventors: Adrian Napoles, Bellevue, WA (US); Christopher Raymond Grajewski, Sammamish, WA (US); Andreas Caduff, Clyde Hill, WA (US); David Heckerman, Bellevue, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 903 days.

(21) Appl. No.: 17/155,485

(22) Filed: Jan. 22, 2021

(51) Int. Cl.
| | |
|---|---|
| *A61B 6/00* | (2024.01) |
| *A61B 5/01* | (2006.01) |
| *G16H 40/67* | (2018.01) |
| *H01Q 1/27* | (2006.01) |
| *H04B 7/06* | (2006.01) |

(52) U.S. Cl.
CPC .............. *A61B 5/01* (2013.01); *A61B 6/4417* (2013.01); *G16H 40/67* (2018.01); *H01Q 1/273* (2013.01); *H04B 7/0602* (2013.01)

(58) Field of Classification Search
CPC ........ A61B 5/01; A61B 6/4417; G16H 40/67; H01Q 1/273; H04B 7/0602
See application file for complete search history.

(56) References Cited

U.S. PATENT DOCUMENTS 11,650,625 B1 * 5/2023 Grajewski .............. G10L 25/78
700/1

2002/0019586 A1 * 2/2002 Teller ...................... H04Q 3/00
128/903

OTHER PUBLICATIONS

"0.1 GHz to 3 GHZ, 1 dB LSB, 5-Bit, GaAs Digital Attenuator—Data Sheet HMC470A", Analog Devices Inc., 2017, pp. 1-11. Retrieved from the Internet: URL: https://www.analog.com/media/en/technical-documentation/data-sheets/hmc470A.pdf.

"ADS124S0x Low-Power, Low-Noise, Highly Integrated, 6- and 12-Channel, 4-kSPS, 24-Bit, Delta-Sigma ADC with PGA and Voltage Reference", Texas Instruments Inc., ADS124S06, ADS124S08, SBAS660C—Aug. 2016—Revised Jun. 2017, 113 pages. Retrieved from the Internet: URL: https://www.ti.com/general/docs/suppproductinfo.tsp?distId=10&gotoUrl=http%3A%2F%2Fwww.ti.com%2Flit%2Fgpn%2Fads124s06.

"Chip Coil (Chip Inductors) LQG15HN _02 Series Reference Specification", Spec No. JELF243B-0009T-01, Murata Mfg. Co., Ltd, pp. 1-11. Retrieved from the Internet: URL: https://search.murata.co.jp/Ceramy/image/img/P02/JELF243B-0009.pdf.

(Continued)

*Primary Examiner* — Jay Patidar
(74) *Attorney, Agent, or Firm* — Lindauer Law, PLLC

(57) ABSTRACT

Data about concentration of one or more types of molecules present within a human body are determined noninvasively using radio frequency (RF) signals. Signals at several different frequencies at very low power levels are emitted using an antenna mounted to a wearable device. Operating values, such as changes to the impedance of the antenna resulting from interaction between the RF signals and the user, are associated with the concentration of one or more types of molecules within the user. These changes in impedance may be relatively small. Circuitry in the device determines internal impedance of the circuitry, compensating for internal impedances and improving overall accuracy of the measured impedance resulting from interaction with the user.

20 Claims, 11 Drawing Sheets

(56) References Cited

OTHER PUBLICATIONS

"HMC550 / 550 E—GaAs MMIC SPST Failsafe Switch, DC-6 GHZ", Analog Devices, pp. 14-1 to 14-6. Retrieved from the Internet: URL: https://www.analog.com/media/en/technical-documentation/data-sheets/hmc550.pdf.

"i.MX RT500 and i.MX RT600 Crossover MCUs", NXP 2020, Document No. IMXRT500RT600FS Rev 0, 2 pages. Retrieved from the Internet: URL: https://www.nxp.com/docs/en/fact-sheet/IMXRT500RT600FS.pdf.

"SM RF Synthesizer with Integrated VCOs for Wireless Communications", Si4136/Si4126, Silicon Labs, pp. 1-34. Retrieved from the Internet: URL: https://media.digikey.com/pdf/Data%20Sheets/Silicon%20Laboratories%20PDFs/Si4136_Si4126Rev2014.pdf.

"LF-2.7 GHz RF/IF Gain and Phase Detector—AD8302", Analog Devices, Inc., 2018, pp. 1-23. Retrieved from the Internet: URL: https://www.analog.com/media/en/technical-documentation/data-sheets/AD8302.pdf.

"LMV3xx Low-Voltage Rail-to-Rail Output Operational Amplifier", Texas Instruments, Inc., LMV321, LMV324, LMV358, SLOS263X—Aug. 1999—Revised May 2020, 51 pages. Retrieved from the Internet: URL: https://www.ti.com/lit/ds/symlink/lmv321.pdf.

"Low Power 250 MSPS 10-Bit DAC 1.8 V CMOS Direct Digital Synthesizer—Data Sheet AD9913", Analog Devices, Inc., pp. 1-32. Retrieved from the Internet: URL: https://www.analog.com/media/en/technical-documentation/data-sheets/AD9913.pdf.

"Mutlilayer Diplexer for 699-960MHz / 1427-2690MHz", RF Components, TDK, Jul. 2018, 7 pages. Retrieved from the Internet: URL: https://product.tdk.com/info/en/documents/data_sheet/rf_dpx_dpx202690dt-4060a1_en.pdf.

"PIN diode", Wikipedia, Nov. 23, 2020, 4 pages. Retrieved from the Internet: URL: https://en.wikipedia.org/wiki/PIN_diode.

"The Pin Diode Circuit Designers' Handbook", Microsemi-Watertown, 1998, 137 pages. Retrieved from the Internet: URL: https://qsl.net/n9zia/pdf/pin_diode_handbook.pdf.

\* cited by examiner

RADIO FREQUENCY BIOSENSOR WITH INTEGRATED COMPENSATION

BACKGROUND

Physiological data may be used to help a user manage their health, make more informed decisions, and improve the quality of their life. For example, physiological data such as hydration level, glucose concentration, and so forth may be useful for health management.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
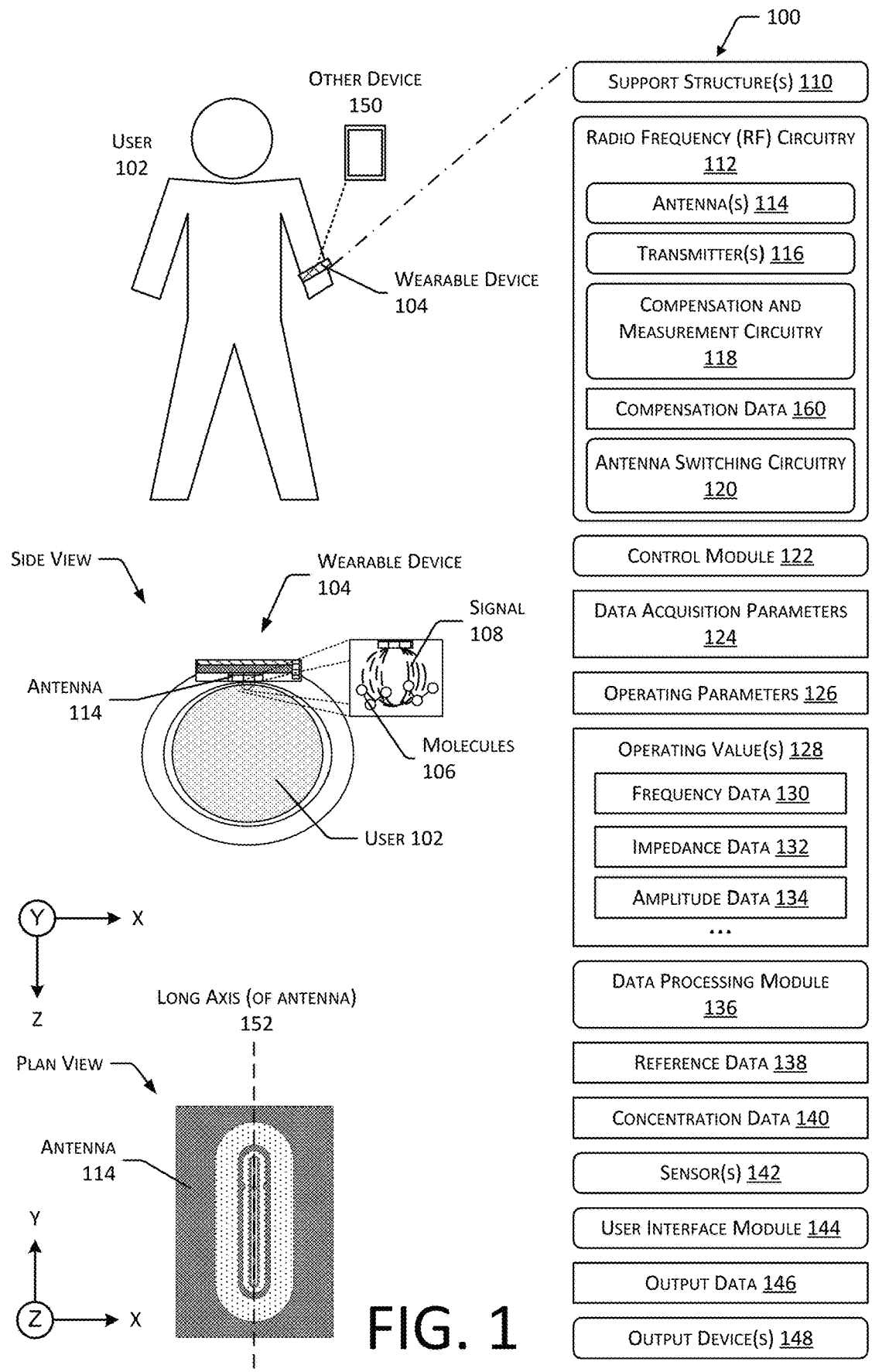
FIG. 1 is an illustrative system that includes a wearable device with an antenna that uses radio frequency signals to determine molecular concentrations of molecules of interest in the user, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

The human body utilizes many different kinds of molecules to function. For example, glucose provides energy for cellular activity while water provides a medium to carry molecules such as glucose and also acts as a reactant. Other molecules may be introduced into the body. For example, alcohol may be consumed, carbon monoxide may be inhaled, a pesticide may be absorbed through the skin, and so forth.

Information about the concentration of one or more types of molecules within the tissues of the body is useful in many situations. For example, a person who is diabetic needs to know the concentration of glucose in their blood in order to keep that concentration in a healthy range. In another example, an athlete needs to make sure they are sufficiently hydrated to maximize their physical performance and avoid injury due to dehydration. Continuing the example, the athlete may also want to monitor their sodium and potassium levels to maintain an optimal level of electrolytes.

Traditionally, information about the concentration of one or more types of molecules has been obtained through invasive measurement of a sample obtained from the person. For example, to measure glucose levels a sample of blood is taken and applied to a chemical test strip. In another example, a rough estimate of dehydration can be obtained by assessing skin turgor, such as by pinching the skin on the back of the hand. However, traditional methods have significant drawbacks. Obtaining samples of blood or other tissues within the body requires piercing the skin, injuring the person and introducing a possibility of infection. Additionally, such testing can be costly due to special handling considerations, use of consumables such as reagents, and so forth. Mechanical measurements, such as assessment of skin turgor, lack precision.

Described in this disclosure is a radio frequency (RF) biosensor comprising RF circuitry to acquire data that is then used to non-invasively measures molecular concentration of one or more types of molecules within a user. The RF circuitry includes a transmitter that generates a very low power RF signal that is emitted from an antenna, with the electromagnetic field from the antenna impinging upon a portion of the user. The presence of different concentrations of molecules will interact with this electromagnetic field and introduce changes in operating values, such as impedance of the antenna. In one implementation, measurement circuitry may determine changes in impedance of the antenna due to changes in the nearby portion of the user that are within the electromagnetic field from the antenna.

Many factors may affect the measurement of the operating values. If uncorrected, these factors impair the accuracy of the measurement. In implementations where the operating value measured is impedance, changes in power supply voltage, variation in manufacture, component aging, temperature, and so forth may change the measured impedance. For example, variations in power supply voltage due to changes in battery charge level, temperature of components in the power supply, current draw, and so forth may also change the value of the impedance measured. In another example, stray impedance may result from reactance due to stray inductances or capacitances of conductive traces on a printed circuit board (PCB).

Compensation and measurement circuitry determines the impedance of at least a portion of the circuitry from the transmitter to the load selection circuitry. The load selection circuitry allows selective connection of the antenna or one or more known reference loads to the output of the transmitter. For example, the known reference loads may comprise three impedance devices, each with a different known value. For example, the impedance device may comprise one or more of a resistor, capacitor, inductor, or other elements. Each of these impedance devices provides a known impedance to a signal. The compensation and measurement circuitry may include a vector voltmeter or other circuitry that determines a voltage of a signal generated by the transmitter while connected to the antenna or the one or more reference loads. The compensation and measurement circuitry comprises as a voltage divider with voltage measured by the vector voltmeter and particular reference loads selected by using RF switches. A set of voltage values are determined, each voltage value representing a voltage measured while a particular one of the known reference loads is connected to the transmitter. The set of voltage values may then be used to solve for and determine compensation data. The compensation data is indicative of the combined impedances presented by at least a portion of the circuitry.

Once known, the compensation data may be used to generate corrected impedance data. For example, the compensation and measurement circuitry may determine a compensation value at a first time that is indicative of a first impedance value. At a second time, a second impedance value indicative of the impedance of the antenna while measuring a portion of the user may be determined. A third impedance value may be determined by subtracting the first impedance value from the second impedance value. The third impedance value thus compensates for variations in measurement of the impedance of the at least a portion of the circuitry that may result from factors such as actual variations in the impedance, power supply variations, and so forth. The third impedance value may then be used to determine concentration data indicative of the concentration of one or more types of molecule in the user.

In one implementation, the antenna may include a plurality of antenna elements. In this implementation, antenna switching circuitry between the antenna and the load selection circuitry allows different combinations of antenna elements to be connected to the transmitter. By selectively using particular antenna elements, different electromagnetic field shapes may be produced. These different field shapes extend different distances from the antenna, allowing information to be obtained about different depths within the user.

During operation of the system to determine concentration data, the compensation and measurement circuitry may determine compensation data using the known reference loads. The output from the transmitter is then connected to the antenna. The antenna switching circuitry may be used to selectively connect a particular set of antenna elements to the transmitter. The RF transmitter generates a first signal at a first frequency that is emitted from the set of antenna elements of the antenna. Measurement circuitry determines one or more operating values associated with the operation of the RF transmitter. The operating values may include information such as frequency data indicative of the frequency of the generated signal, impedance data indicative of impedance presented by the antenna, amplitude data, and so forth. For example, the measurement circuitry may determine an impedance presented by the antenna to the first signal. At different times, different sets of antenna elements may be used to acquire information about different depths within the user. The compensation data may be applied to initial or "raw" operating values, or may be applied to produce the operating values.

The RF circuitry may utilize different frequencies at different times. For example, the transmitter may comprise one or more transmitters to generate signals in different frequency bands, providing operating values for the different bands. For example, the first signal may be transmitted at 50 megahertz (MHz), a second signal at 5 gigahertz (GHz), a third signal at 5 kilohertz (KHz), a fourth signal at 100 GHz, and so forth.

The operating values, based on the compensated values, may be compared to reference data to determine one or more of presence of or concentration of one or more types of molecules present within the user. In one implementation, the impedance presented at different frequencies and corrected using the compensation data may be used to determine a concentration of a type of molecule, such as glucose. For example, the molecular concentration data may describe a linear relationship between impedances at particular frequencies and glucose concentration. In other implementations, the concentration of other types of molecules may be determined. For example, the concentration of water may be determined, providing information about a hydration level of the user.

Overall exposure to RF signals is limited, as the output power is extremely low and duration of the RF signals may be very short. For example, the modulation of the signals may be a continuous wave with a total duration of less than 1 millisecond (ms) and with a transmitter output power of 0 decibel-milliwatts (dBm). The sampling frequency, that is how often the RF signals are transmitted to gather data, may also be low, further reducing RF exposure. For example, the system may transmit signals once every six minutes, producing sets of ten samples per hour with each set comprising operating value data for the various frequency bands.

The compensation and measurement circuitry may be operated to determine the compensation data responsive to various conditions, events, or changes. For example, the compensation data may be determined before every instance of determining operating values. In another example, the compensation data may be generated once every 60 minutes. In yet another example, if a change in temperature associated with the device from a first time to a second time that exceeds a threshold value may trigger the determination of compensation data. In still another example, the compensation data may be determined responsive to one or more of the operating values being outside of an expected range of values. In this example, the compensation data may be applied retroactively to the operating values previously determined.

By using the system described in this disclosure, information about the concentration of various types of molecules at different depths within the user may be determined non-invasively. The ability to quickly and accurately determine the compensation data improves the quality of the measurements acquired, improving the quality of the resulting information such as concentration data. The information provided by the system may be used to help diagnose, treat, or inform the user as to their physiological status. By acting on this information, the overall health of the user may be improved.

Illustrative System

FIG. 1 is an illustrative system 100 that may include a user 102 and a wearable device 104 that uses radio frequency (RF) signals to determine molecular concentrations of molecules of interest in at least a portion of the user's body, according to one implementation.

The user 102 may have one or more devices on or about their person, such as the wearable device 104. The wearable device 104 may be implemented in various physical form factors including, but not limited to, the following: wrist bands, torcs, arm bands, ankle bands, abdominal straps, and so forth. In other implementations the device may be implemented in other physical form factors. For example, the device may be a tabletop unit, handheld unit, may be integrated into an operating table, hospital bed, wheelchair, and so forth.

The user's 102 body contains one or more different types of molecules 106. For example, the blood of the user 102 may include glucose, water, creatinine, and so forth. Sometimes the body may include molecules 106 that are exogenous. For example, if the user 102 consumes alcohol, inhales carbon monoxide, absorbs a pesticide through the skin, and so forth, presence or concentration of those types of molecules 106 may be present in the dermis, within the blood, or other tissues within the body. As described below, a radio frequency (RF) signal 108 may be used to determine information about one or more molecules 106.

The wearable device 104 may include at least one support structure 110 that supports one or more of the following components. For example, the wearable device 104 may comprise a housing or capsule that is attached to a wrist band, allowing the wearable device 104 to be retained on the wrist of the user 102 as shown in FIG. 1. In another example, the wearable device 104, or a portion thereof, may comprise an adhesive patch to adhere to the user 102 during operation. Also shown in FIG. 1 is a side view of the wearable device 104 as shown worn on the arm. An enlarged view shows the signal 108 and the molecules 106.

The wearable device 104 includes radio frequency (RF) circuitry 112 that includes one or more antennas 114, one or more transmitters 116, compensation and measurement circuitry 118, antenna switching circuitry 120, and may include other circuitry. The antennas 114 may comprise one or more antenna elements in particular arrangements. For example, the antenna elements may comprise a first antenna element and one or more additional antenna elements that are arranged around the first antenna element. The overall arrangement of the antenna 114 may appear as an elongated oval, with a long axis 152 extending through a long axis of the elongated oval. In some implementations, during use the long axis 152 of the antenna may be arranged to parallel a long axis of an arm or leg of the user 102. This arrangement between the antenna 114 and the user 102 may improve the quality of data obtained by minimizing variations in output of the operating values due to motion of the user 102. The arrangement of antenna elements is discussed in more detail below with regard to FIGS. 4 and 5.

The compensation and measurement circuitry 118 determines compensation data 160. The compensation data 160 may characterize at least a portion of the RF circuitry 112. For example, the compensation data 160 may be indicative of the impedance presented by circuitry including the transmitter 116 and load selection circuitry within the compensation and measurement circuitry 118. The compensation and measurement circuitry 118 provides a voltage divider circuit for the output of the transmitter 116, with one leg of the circuit being load selection circuitry and associated reference loads. The load selection circuitry allows selective connection of different known reference loads to the output of the transmitter 116 that is producing a signal. While a given reference load is connected, a vector voltmeter or other device measures the voltage of the signal. A set of voltages are acquired while the transmitter 116 is connected to the different known reference loads. Based on the values of the known reference loads and the set of voltages, an impedance value is determined. This impedance value is representative of actual impedances of the circuitry between the transmitter 116 and at least the load selection circuitry, as well as changes in impedance measurement that may be due to other factors, such as changes in power supply voltage. Operation of the compensation and measurement circuitry 118 is discussed in more detail with regard to FIGS. 9-10.

The antenna switching circuitry 120 selectively couples the output from the transmitter 116, as provided via the compensation and measurement circuitry, to one or more of the antenna elements in the antenna 114. The switching circuitry is discussed in more detail with regard to FIG. 7.

The transmitter 116 is configured to generate an RF signal 108. The transmitter 116 may be able to generate RF signals 108 at one or more frequencies, in one or more frequency bands or ranges, and so forth. For example, the transmitter 116 may be able to generate RF signals 108 at one or more of the 1 kHz, 50 MHz, 5 GHZ, or other bands. The RF signal 108 that is generated may be modulated with a continuous wave.

During operation to determine a measurement associated with the user 102, the transmitter 116 provides the RF signal 108 to the compensation and measurement circuitry 118 that in turn provides the RF signal 108 to the antenna switching circuitry 120. The antenna switching circuitry 120 then directs the RF signal 108 to a set of the one or more of the antenna elements of the antenna 114. For example, output from the transmitter 116 may be connected to a first antenna element in the antenna 114 at a first time. The antenna 114 emits the signal 108 which then impinges on the body of the user 102 while the wearable device 104 is being worn or held close to the user 102. At a second time, a second set of the one or more antenna elements of the antenna 114 may be used.

The compensation and measurement circuitry 118 determines one or more operating values 128 associated with one or more of the operation of the transmitter 116, the load presented by the antenna 114, and so forth. The operating values 128 may include information such as frequency data 130 indicative of the frequency of the generated signal 108, impedance data 132 indicative of impedance presented by the antenna 114 comprising the set of antenna elements connected via the antenna switching circuitry 120, amplitude data 134 indicative of an amplitude of the RF signal 108, and so forth. For example, the compensation and measurement circuitry 118 may determine an impedance presented by the antenna 114 to the first signal at 50 MHz.

While a transmitter 116 is shown, it is understood that in other implementations the RF circuitry 112 may include a plurality of transmitters, digital synthesizers, other components such as receiver, transceiver, and so forth.

A control module 122 may be used to direct operation of the RF circuitry 112 or other components. For example, the control module 122 may comprise a hardware processor (processor) executing instructions that operate the compensation and measurement circuitry 118 to determine compensation data or generate operating values 128 associated with the antenna 114, antenna switching circuitry 120 to connect a particular set of antenna elements of the antenna 114 to the transmitter 116, operate the transmitter 116 to transmit particular signals at particular frequencies at particular times, acquire operating values 128 during operation of the transmitter 116, and so forth.

The control module 122 may use one or more data acquisition parameters 124 to control operation. For example, the data acquisition parameters 124 may specify a sample frequency that indicates how often to transmit signals, sample depth within the user 102 to be used, and so forth. In some implementations the data acquisition parameters 124 may be specific to a particular type of molecule 106 that is being detected. For example, the data acquisition parameters 124 for glucose may have a first sample depth that is different from a second sample depth used for organophosphates. The data acquisition parameters 124 may reference specific operating parameters 126.

The operating parameters 126 may specify one or more of frequency, output power, modulation, signal duration, particular antenna elements used to emit the signal 108, particular antenna elements used to acquire the signal 108, when to determine compensation data 160, and so forth. For example, the operating parameters 126 may specify that a signal is to be transmitted with a center frequency of 50 MHz at 0 dBm, continuous wave (CW) modulation, particular sets of antenna elements to use to obtain data from the desired depths, and so forth. In another example, the operating parameters 126 may specify that the compensation data 160 is to be determined before every nth operation to determine operating values 128, where n is a non-zero positive integer.

The operating parameters 126 may relate a sample depth specified by the data acquisition parameters 124 to a particular antenna configuration. For example, the data acquisition parameters 124 may indicate a depth in terms of linear measurement such as millimeters or with a relative indicator such as "shallow", "medium", or "deep". Responsive to the data acquisition parameters 124, the control module 122 may determine operating parameters 126 that are indicative of a particular antenna configuration. For example, a "shallow" sample depth may correspond to an antenna configuration or set of antenna elements in which the first antenna element is connected to the transmitter 116 and used to emit the signal 108. In comparison, a "deep" sample depth may correspond to an antenna configuration or set of antenna elements in which the first antenna element, a second antenna element, and a third antenna element are simultaneously connected to the transmitter 116 and used to emit the signal 108.

Once the operating parameters 126 have been determined, the control module 122 or another component may operate the circuitry in the wearable device 104. For example, the control module 122 may operate at a first time the compensation and measurement circuitry 118 to determine compensation data 160. The control module 122 may then, at a second time, operate RF circuitry 112 to selectively connect a first set of antenna elements to the transmitter 116, operate the transmitter 116 to generate a first signal 108 at a first frequency, and operate the compensation and measurement circuitry 118 to acquire a first impedance value. Continuing the example, at a third time the antenna switching circuitry 120 may be operated to selectively connect a second set of antenna elements to the transmitter 116, operate the transmitter 116 to generate a second signal 108 at a second frequency, and operate the compensation and measurement circuitry 118 to acquire a second impedance value. The first impedance value and the second impedance value may include, or otherwise be adjusted based on the compensation data 160.

As the RF signals 108 as emitted by the antenna 114 impinge on the body of the user 102, they are affected by the molecules 106 therein. Various interactions take place between the signals 108 and the molecules 106. For example, the presence of glucose in the body within the volume encompassed by the electromagnetic field produced by the antenna 114 during operation of the transmitter 116 may result in a change in impedance that the antenna 114 presents to the transmitter 116. As described below, a presence or concentration of a type of molecule 106 may be determined based on the impedance or other operating values.

A data processing module 136 may use one or more of the operating parameters 126 of the transmitted signal(s) 108 or the operating values 128 as input. The data processing module 136 may also access reference data 138. The reference data 138 comprises information that, for a particular type of molecule 106, associates one or more operating values 128 with information such as concentration of the particular type of molecule 106. The reference data 138 may be general or specific to a particular user 102. For example, the reference data 138 may be generated and associated with particular user 102(1) "Pat".

The data processing module 136 may use the operating value(s) 128 and the reference data 138 to determine molecular concentration data 140. The molecular concentration data 140 may specify a mass per unit volume. For example, the operating value 128 indicates the impedance value at a particular frequency is 51.7 ohms at 50 MHz. This value may be used as input to the reference data 138 which corresponds to molecular concentration data 140 indicative of a mass per volume, such as a glucose concentration of 159 milligrams per deciliter (mg/dl).

As described below in more detail, the operating values 128 may be obtained for a plurality of different frequencies and may be obtained using a variety of different sets of antenna elements of the antenna 114 to emit the signals 108. The operating values 128 may be used to determine the molecular concentration data 140 for one or more different types of molecules 106. For example, the molecular concentration data 140 may indicate the concentration of glucose and water in the body of the user 102.

The wearable device 104 may include, or receive data from, one or more other sensors 142. For example, a temperature sensor may be used to provide an indication of the body temperature of the user 102. The body temperature may then be used as an input to the data processing module 136 to improve the accuracy of the molecular concentration data 140. These sensors 142 are discussed in more detail below with regard to FIG. 2. In other implementations data from the sensors 142 may be obtained to provide other information about physiological status, activity level, and so forth.

Output from the sensors 142 may also be used to determine operation of the data processing module 136. For example, the sensors 142 may include one or more accelerometers. If the accelerometers detect motion that exceeds a threshold value, the data processing module 136 may be operated to determine molecular concentration data 140. For example, if the user 102 has been running, the system 100 may operate to determine glucose concentration. In another example, if the motion of the user 102 is less than a threshold value, the data processing module 136 may be operated to determine molecular concentration data 140. For example, if no movement has been detected for 2 minutes, such as if the user 102 is asleep or unconscious, the data processing module 136 may be operated to determine molecular concentration data 140.

A user interface module 144 may be configured to use the molecular concentration data 140 and produce output data 146. For example, based on the molecular concentration data 140 indicating that the blood glucose level is below a threshold value, output data 146 may be generated. One or more output devices 148 may be used to present a user interface based on at least a portion of the output data 146. Continuing the example, the user interface module 144 may produce output data 146 that comprises instructions to operate a speaker to present an audible prompt indicating the low blood glucose level. In another example, the output data 146 may be provided to an other device 150. For example, the wearable device 104 may be connected via Bluetooth or another wireless protocol to a smartphone, wireless access point, in vehicle computer system, or other device. Based on the output data 146 the other device 150 may present an output to the user 102, alert someone else, modify operation of another device, and so forth. For example, if the wearable device 104 provides data to a vehicle that indicates the user 102 in the driver's seat has a concentration of alcohol that exceeds a threshold value, the vehicle may be prevented from moving, or may only be able to operate in a fully autonomous mode.

Figure 2:
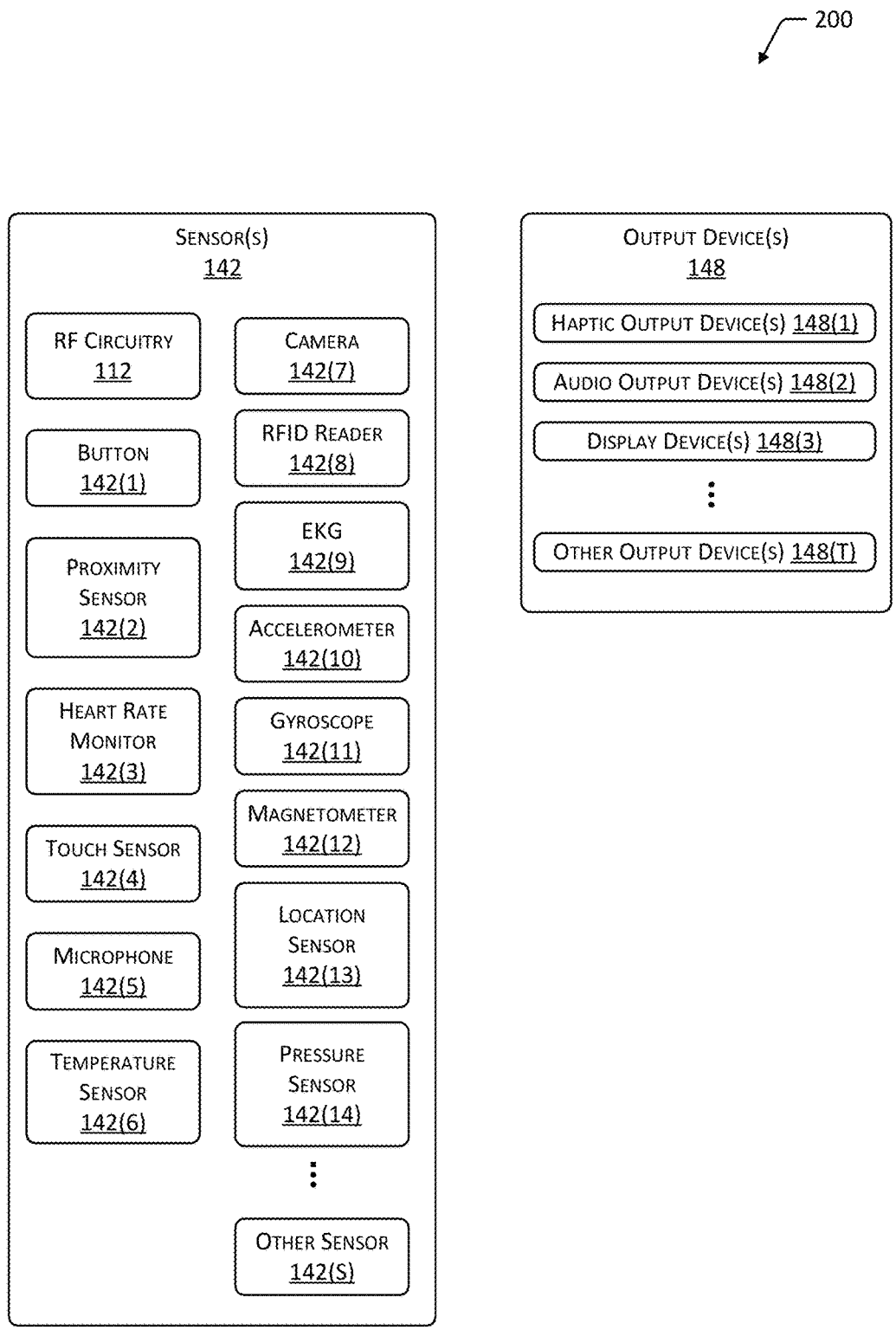
FIG. 2 illustrates a block diagram of sensors and output devices that may be used by computing device(s) during operation, according to one implementation.

FIG. 2 illustrates a block diagram 200 of sensors 142 and output devices 148 that may be used by the devices of the system 100 during operation.

The one or more sensors 142 may be integrated with or internal to the wearable device 104 or the other device 150. For example, the sensors 142 may be built-in to the wearable device 104 during manufacture. In other implementations, the sensors 142 may be part of another device which is in communication with the wearable device 104. For example, the sensors 142 may comprise a device external to, but in communication with, the wearable device 104 using Bluetooth, Wi-Fi, 4G, 5G, LTE, ZigBee, Z-Wave, or another wireless or wired communication technology.

The sensors 142 may include the RF circuitry 112.

The one or more sensors 142 may include one or more buttons 142(1) that are configured to accept input from the user 102. The buttons 142(1) may comprise mechanical, capacitive, optical, or other mechanisms. For example, the buttons 142(1) may comprise mechanical switches configured to accept an applied force from a touch of the user 102 to generate an input signal.

A proximity sensor 142(2) may be configured to provide sensor data 324 indicative of one or more of a presence or absence of an object, a distance to the object, or characteristics of the object. The proximity sensor 142(2) may use optical, electrical, ultrasonic, electromagnetic, or other techniques to determine a presence of an object. For example, the proximity sensor 142(2) may comprise a capacitive proximity sensor configured to provide an electrical field and determine a change in electrical capacitance due to presence or absence of an object within the electrical field.

A heart rate monitor 142(3) or pulse oximeter may be configured to provide sensor data 324 that is indicative of a cardiac pulse rate, data indicative of oxygen saturation of the user's 102 blood, and so forth. For example, the heart rate monitor 142(3) may use an optical emitter such as one or more light emitting diodes (LEDs) and a corresponding optical detector such as a photodetector to perform photoplethysmography, determine cardiac pulse, determine changes in apparent color of the blood of the user 102 resulting from oxygen binding with hemoglobin in the blood, and so forth.

The sensors 142 may include one or more touch sensors 142(4). The touch sensors 142(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 142(5) may be configured to acquire information about sound present in the environment. In some implementations, arrays of microphones 142(5) may be used. These arrays may implement beamforming techniques to provide for directionality of gain. The one or more microphones 142(5) may be used to acquire audio data, such as speech from the user 102.

A temperature sensor (or thermometer) 142(6) may provide information indicative of a temperature of an object. The temperature sensor 142(6) in may be configured to measure ambient air temperature proximate to the user 102, the body temperature of the user 102, and so forth. The temperature sensor 142(6) may comprise a silicon bandgap temperature sensor, thermistor, thermocouple, or other device. In some implementations, the temperature sensor 142(6) may comprise an infrared detector configured to determine temperature using thermal radiation.

The sensors 142 may include one or more cameras 142(7). The cameras 142(7) may comprise a charge couple device, complementary oxide semiconductor, or other image sensor that is able to acquire images.

One or more radio frequency identification (RFID) readers 142(8), near field communication (NFC) systems, and so forth, may also be included as sensors 142. The user 102, objects around the computing device, locations within a building, and so forth, may be equipped with one or more radio frequency (RF) tags. The RF tags are configured to emit an RF signal. In one implementation, the RF tag may be an RFID tag configured to emit the RF signal upon activation by an external signal. For example, the external signal may comprise a RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

The sensors 142 may include an electrocardiograph (EKG) 142(9) that is configured to detect electrical signals produced by the heart of the user 102.

The sensors 142 may include one or more accelerometers 142(10). The accelerometers 142(10) may provide information such as the direction and magnitude of an imposed acceleration. Data such as rate of acceleration, determination of changes in direction, speed, and so forth, may be determined using the accelerometers 142(10).

A gyroscope 142(11) provides information indicative of rotation of an object affixed thereto. For example, the gyroscope 142(11) may indicate whether the device has been rotated.

A magnetometer 142(12) may be used to determine an orientation by measuring ambient magnetic fields, such as the terrestrial magnetic field. For example, output from the magnetometer 142(12) may be used to determine whether the device containing the sensor 142, such as a computing device, has changed orientation or otherwise moved. In other implementations, the magnetometer 142(12) may be configured to detect magnetic fields generated by another device.

A location sensor 142(13) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 142(13) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 142(13) may be omitted or operate in conjunction with an external resource such as a cellular network operator providing location information, or Bluetooth beacons.

A pressure sensor 142(14) may provide information about the pressure between a portion of the wearable device 104 and a portion of the user 102. For example, the pressure sensor 142(14) may comprise a capacitive element, strain gauge, spring-biased contact switch, or other device that is used to determine the amount of pressure between the user's 102 arm and an inner surface of the wearable device 104 that is in contact with the arm. In some implementations the pressure sensor 142(14) may provide information indicative of a force measurement, such as 0.5 Newtons, a relative force measurement, or whether the pressure is greater than a threshold value.

In some implementations, operation of one or more components in the wearable device 104 may be based at least in part on information from the pressure sensor 142(14). For example, based on data provided by the pressure sensor 142(14) a determination may be made as to whether at least a portion of the wearable device 104 is in contact with the user 102 or another object. Continuing the example, if the pressure indicated by the pressure sensor 142(14) exceeds a threshold value, the wearable device 104 may be determined to be in contact with the user 102. Based on this determination that the wearable device 104 is in contact with the user 102, one or more of the transmitter 116, receiver, sensors 142, and so forth may be operated. Likewise, data from the pressure sensor 142(14) may be used to determine the wearable device 104 is not in sufficient physical contact with the user 102. As a result, one or more of the transmitter 116, a receiver, sensors 142, and so forth may be turned off.

The sensors 142 may include other sensors 142(S) as well. For example, the other sensors 142(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 142 may include hardware processors, memory, and other elements configured to perform various functions. Furthermore, the sensors 142 may be configured to communicate by way of the network or may couple directly with the computing device.

The computing device may include or may couple to one or more output devices 148. The output devices 148 are configured to generate signals which may be perceived by the user 102, detectable by the sensors 142, or a combination thereof.

Haptic output devices 148(1) are configured to provide a signal, which results in a tactile sensation to the user 102. The haptic output devices 148(1) may use one or more mechanisms such as electrical stimulation or mechanical displacement to provide the signal. For example, the haptic output devices 148(1) may be configured to generate a modulated electrical signal, which produces an apparent tactile sensation in one or more fingers of the user 102. In another example, the haptic output devices 148(1) may comprise piezoelectric or rotary motor devices configured to provide a vibration that may be felt by the user 102.

One or more audio output devices 148(2) are configured to provide acoustic output. The acoustic output includes one or more of infrasonic sound, audible sound, or ultrasonic sound. The audio output devices 148(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 148(2).

The display devices 148(3) may be configured to provide output that may be seen by the user 102 or detected by a light-sensitive detector such as an image sensor or light sensor. The output may be monochrome or color. The display devices 148(3) may be emissive, reflective, or both. An emissive display device 148(3), such as using light emitting diodes (LEDs), is configured to emit light during operation. In comparison, a reflective display device 148(3), such as using an electrophoretic element, relies on ambient light to present an image. Backlights or front lights may be used to illuminate non-emissive display devices 148(3) to provide visibility of the output in conditions where the ambient light levels are low.

The display mechanisms of display devices 148(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 148(3) may operate as panels, projectors, and so forth.

The display devices 148(3) may be configured to present images. For example, the display devices 148(3) may comprise a pixel-addressable display. The image may comprise at least a two-dimensional array of pixels or a vector representation of a two-dimensional image.

In some implementations, the display devices 148(3) may be configured to provide non-image data, such as text or numeric characters, colors, and so forth. For example, a segmented electrophoretic display device, segmented LED, and so forth, may be used to present information such as letters or numbers. The display devices 148(3) may also be configurable to vary the color of the segment, such as using multicolor LED segments.

Other output devices 148(T) may also be present. For example, the other output devices 148(T) may include scent/odor dispensers.

Figure 3:
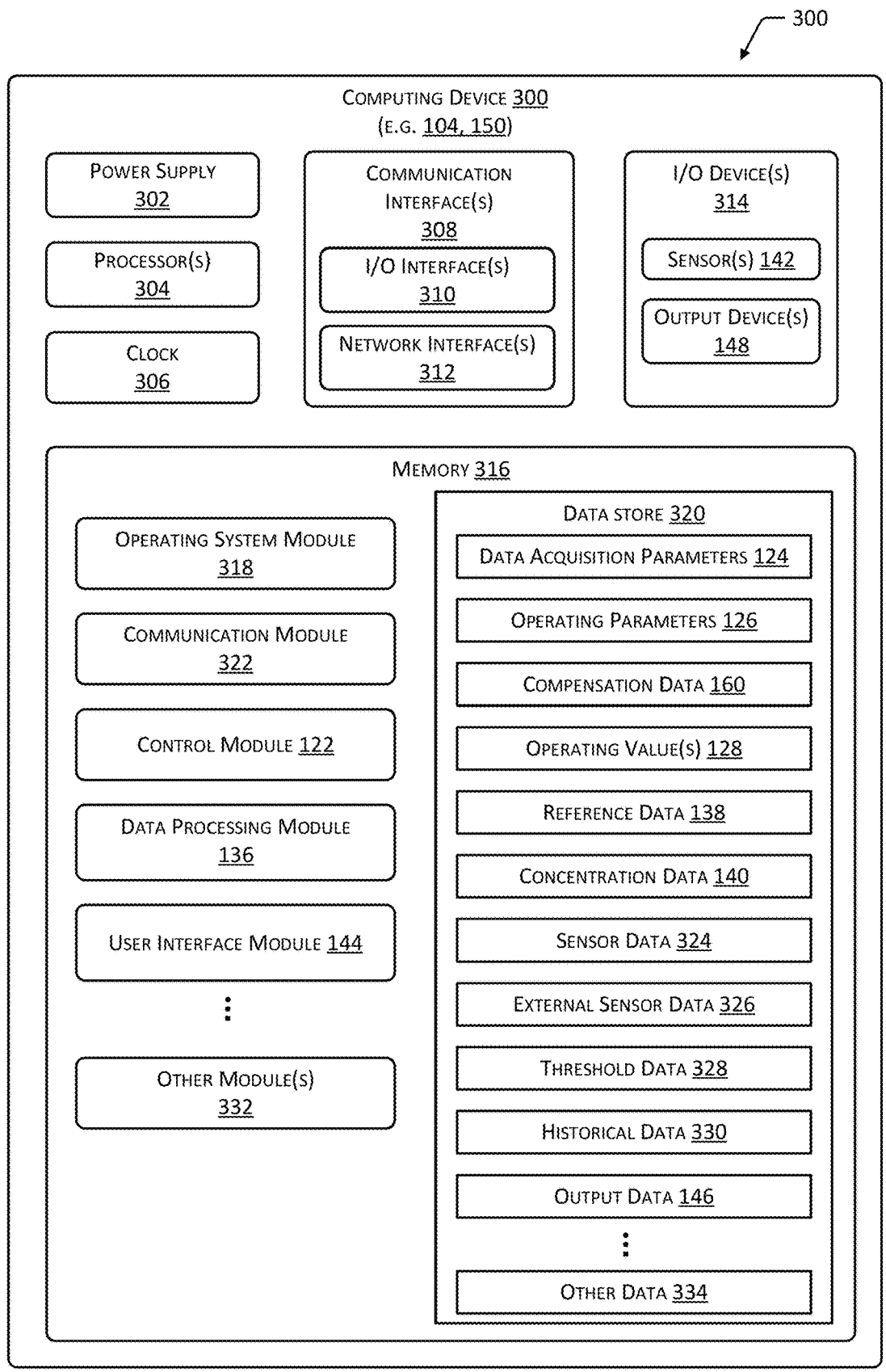
FIG. 3 illustrates a block diagram of a computing device(s) that may be included in or in communication with the measurement device, according to one implementation.

FIG. 3 illustrates a block diagram of a computing device 300 configured to support operation of the system 100. As described above, the computing device 300 may be the wearable device 104, the other device 150, and so forth.

One or more power supplies 302 are configured to provide electrical power suitable for operating the components in the computing device 300. In some implementations, the power supply 302 may comprise a rechargeable battery, fuel cell, photovoltaic cell, power conditioning circuitry, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 308 such as input/output (I/O) interfaces 310, network interfaces 312, and so forth. The communication interfaces 308 enable the computing device 300, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The I/O devices 314 may include input devices such as one or more of a camera 142(7), a sensor 142, keyboard, mouse, scanner, and so forth. The I/O devices 314 may also include output devices 148 such as one or more of a display device 148(3), printer, audio output device 148(2), and so forth. In some embodiments, the I/O devices 314 may be physically incorporated with the computing device 300 or may be externally placed.

The network interfaces 312 are configured to provide communications between the computing device 300 and other devices, such as the sensors 142, routers, access points, and so forth. The network interfaces 312 may include devices configured to couple to wired or wireless personal area networks (PANs), local area networks (LANs), wide area networks (WANs), and so forth. For example, the network interfaces 312 may include devices compatible with Ethernet, Wi-Fi, Bluetooth, ZigBee, 4G, 5G, LTE, and so forth.

The computing device 300 may also include one or more buses or other internal communications hardware or software that allow for the transfer of data between the various modules and components of the computing device 300.

As shown in FIG. 3, the computing device 300 includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the computing device 300. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Washington, USA; the Android operating system from Google Corporation of Mountain View, California, USA; the iOS operating system from Apple Corporation of Cupertino, California, USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including the computing devices 300, network attached storage devices, and so forth.

A communication module 322 may be configured to establish communications with one or more of other computing devices 300, the sensors 142, or other devices 150. The communications may be authenticated, encrypted, and so forth. The communication module 322 may also control the communication interfaces 308.

One or more of the data acquisition parameters 124, operating parameters 126, compensation data 160, operating values 128, reference data 138, or the concentration data 140 may be stored in the memory 316.

The memory 316 may also store the control module 122. As described above, the control module 122 may operate the RF circuitry 112 to produce operating values 128.

The memory 316 may store the data processing module 136. The data processing module 136 uses the operating values 128, the reference data 138, and so forth as input to generate the molecular concentration data 140.

In one implementation, the data processing module 136 may use the compensation data 160, the operating values 128, and the reference data 138 to generate molecular concentration data 140 that is indicative of a concentration of one or more types of molecules 106 in the user 102.

In some implementations, a calibration process may be performed in which an external sensor is used to obtain external sensor data 326 that is indicative of a concentration of a type of molecule 106. For example, a blood glucose meter that uses a sample of a drop of blood may be used as the external sensor. At a contemporaneous time, the RF circuitry 112 may be used to obtain the operating values 128. The external sensor data 326 comprising concentration data from the external sensor may be used in conjunction with the operating values 128 to determine a correspondence between one or more operating values 128 and molecular concentration. This correspondence may be stored as the reference data 138. The reference data 138 may be specific to a particular user 102. For example, the reference data 138 may be specific to user "Pat". In some implementations, the reference data 138 may be processed using one or more techniques to interpolate values between those which have been measured. In some implementations, previously acquired reference data 138 may be used, and a calibration factor may be determined based on the reference data 138.

Threshold data 328 may be stored in the memory 316. The threshold data 328 may be used to designate a threshold to which molecular concentration data 140 may be compared. For example, the threshold data 328 may specify threshold values for particular types of molecules 106. If the molecular concentration data 140 is less than a first threshold or greater than a second threshold, the user interface module 144 may generate an alarm and present that information using the output device 148.

The user interface module 144 provides a user interface using one or more of the I/O devices 314. The user interface module 144 may be used to obtain input from the user 102, present information to the user 102, and so forth. For example, the user interface module 144 may present a graphical user interface on the display device 148(3) and accept user input using the touch sensor 142(4).

Continuing the earlier example, if the molecular concentration data 140 indicates that user's 102 blood glucose level is less than a threshold value, the user interface module 144 may present information indicative of this on the display device 148(3). The user 102 may then take corrective actions, such as consuming glucose to raise their blood sugar level, reducing activity, and so forth.

The computing device 300 may maintain historical data 330. For example, the historical data 330 may comprise the operating values 128, molecular concentration data 140, or data from one or more of the sensors 142 obtained at different times. The historical data 330 may be used to provide information about trends or changes over time. For example, the historical data 330 may comprise an indication of average daily blood glucose levels of the user 102 over a span of several weeks. The user 102 may then use this data to assist in managing their diet and insulin dosage.

Other modules 332 may also be present in the memory 316, as well as other data 334 in the data store 320.

In different implementations, different computing devices 300 may have different capabilities or capacities. For example, the other device 150 may have significantly more processor 304 capability and memory 316 capacity compared to the wearable device 104. In one implementation, the wearable device 104 may determine the operating values 128 and send those values to the other device 150. Other combinations of distribution of data processing and functionality may be used in other implementations.

Figure 4:
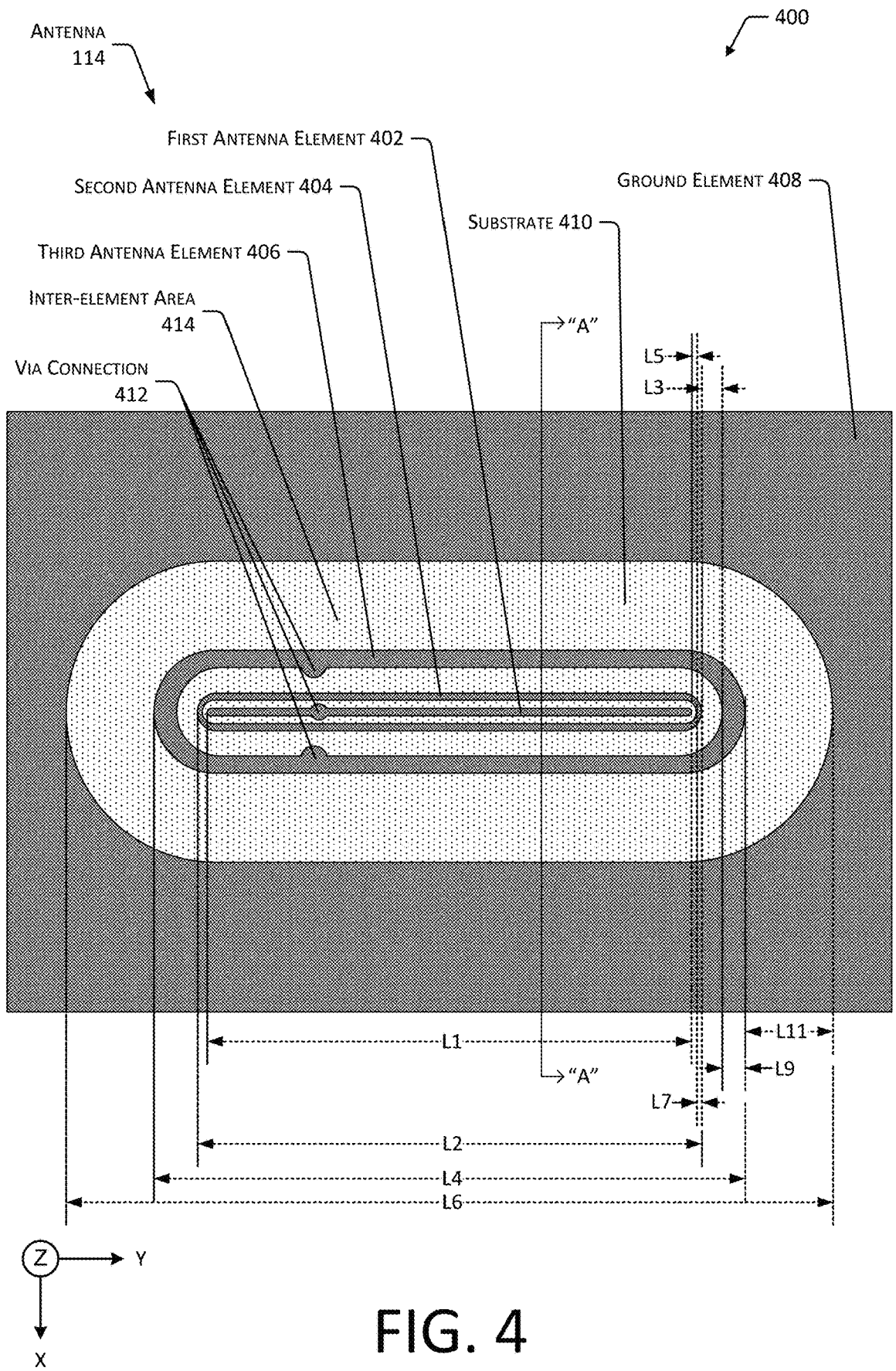
FIG. 4 illustrates one implementation of antenna elements in the antenna.

FIG. 4 illustrates a plan view 400 of one implementation of antenna elements in the antenna 114.

A first implementation of an antenna 114 is shown that comprises a first antenna element 402, a second antenna element 404, a third antenna element 406, and a ground element 408. The antenna 114 may comprise a substrate 410 that is electrically non-conductive. For example, the substrate 410 may comprise an insulator such as plastic or glass. The antenna elements may be on, affixed to, incorporated within, or otherwise maintained by the substrate 410. The substrate 410 may be rigid or flexible. For example, the substrate 410 may comprise a plastic layer upon which the antenna elements have been deposited. In one implementation the antenna 114 may comprise a flexible printed circuit with the antenna elements comprising traces thereon.

The first antenna element 402 may comprise a generally linear structure, having a first width and a first length L1. In the implementation shown here, the first length is greater than the first width. In other implementations, other configurations may be used.

The second antenna element 404 is arranged around the first antenna element 402. The second antenna element 404 has a second width and a second length L2. The second width is greater than the first width and L2 is greater than L1. The third antenna element 406 is arranged around the second antenna element 404. The third antenna element 406 has a third width and a third length L4. The third width is greater than the second width and L4 is greater than L2. A sixth length L6 is shown extending along a long axis of the antenna 114 from a first innermost edge of the ground element 408 at a first end of the long axis to a second innermost edge of the ground element 408 at a second end of the long axis.

A third length L3 is shown that is indicative of a distance or gap between an outermost edge of the first antenna element 402 and interior edge of the second antenna element 404. A fifth length L5 is shown that is indicative of a distance or gap between an outermost edge of the second antenna element 404 and an interior edge of the third antenna element 406. A seventh length L7 is indicative of a width of the second antenna element 404. A ninth length L9 is indicative of a width of the third antenna element 406. In some implementations L9 may be greater than L7. An eleventh length L11 is indicative of a distance or gap between an outermost edge of the third antenna element 406 and an interior edge of the ground element 408.

The ground element 408 is arranged around the third antenna element 406. In this implementation, the first antenna element 402 is linear. The second antenna element 404 forms an elongated oval or "racetrack" pattern with the first antenna element 402 nested within. The third antenna element 406 also forms an elongated oval of larger dimensions with the second antenna element 404 nested within. The edge of the ground element 408 around the third antenna element 406 also describes an elongated oval. For example, a distance between an outermost edge of the third antenna element 406 and an innermost edge of the ground element 408 may be constant. Continuing the example, for a given point on the outermost edge of the third antenna element 406, a tangent may be determined. A distance from the point and perpendicular to the tangent to the innermost edge of the ground element 408 may be constant for all points along the outermost edge of the third antenna element 406.

In the implementation depicted here, the overall arrangement of the antenna elements relative to the ground element 408 and one another is symmetrical with respect to at least two axes. In other implementations, other arrangements may be used. These arrangements may be asymmetrical in overall pattern, size of antenna elements, spacing between antenna elements, and so forth.

Also shown are via connections 412 that comprise enlarged portions of antenna elements to provide for electrical connectivity through vias to feedlines on a backside of the substrate 410 (not shown). For example, portions of the third antenna element 406 and the first antenna element 402 have larger surface areas to provide additional cross sectional areas for connection to the vias.

An inter-element area 414 is shown between two adjacent antenna elements. For example, there is a first inter-element area 414 between the first antenna element 402 and the second antenna element 404, a second inter-element area 414 between the second antenna element 404 and the third antenna element 406, and a third inter-element area 414 between the third antenna element 406 and the ground element 408.

The antenna 114 may comprise two or more antenna elements. While four antenna elements are depicted here, in other implementations the antenna 114 may include more or fewer antenna elements. In some implementations arrays of antennas 114 may be used. The arrays may include antennas 114 with different dimensions.

The dimensions of the antenna elements may be determined based on the sample depth desired during operation. For example, as the area of the antenna 114 increases, the electromagnetic field provided by the antenna 114 during operation may also increase, allowing measurement at increased depth.

One or more of the antenna elements may comprise closed loops as shown here. For example, the first antenna element 402 may comprise a rectangular area or strip while the second antenna element 404 comprises an electrically conductive ring. In other implementations, the second antenna element 402 may have at least one gap or electrically non-conductive region to form a split ring.

Figure 5:
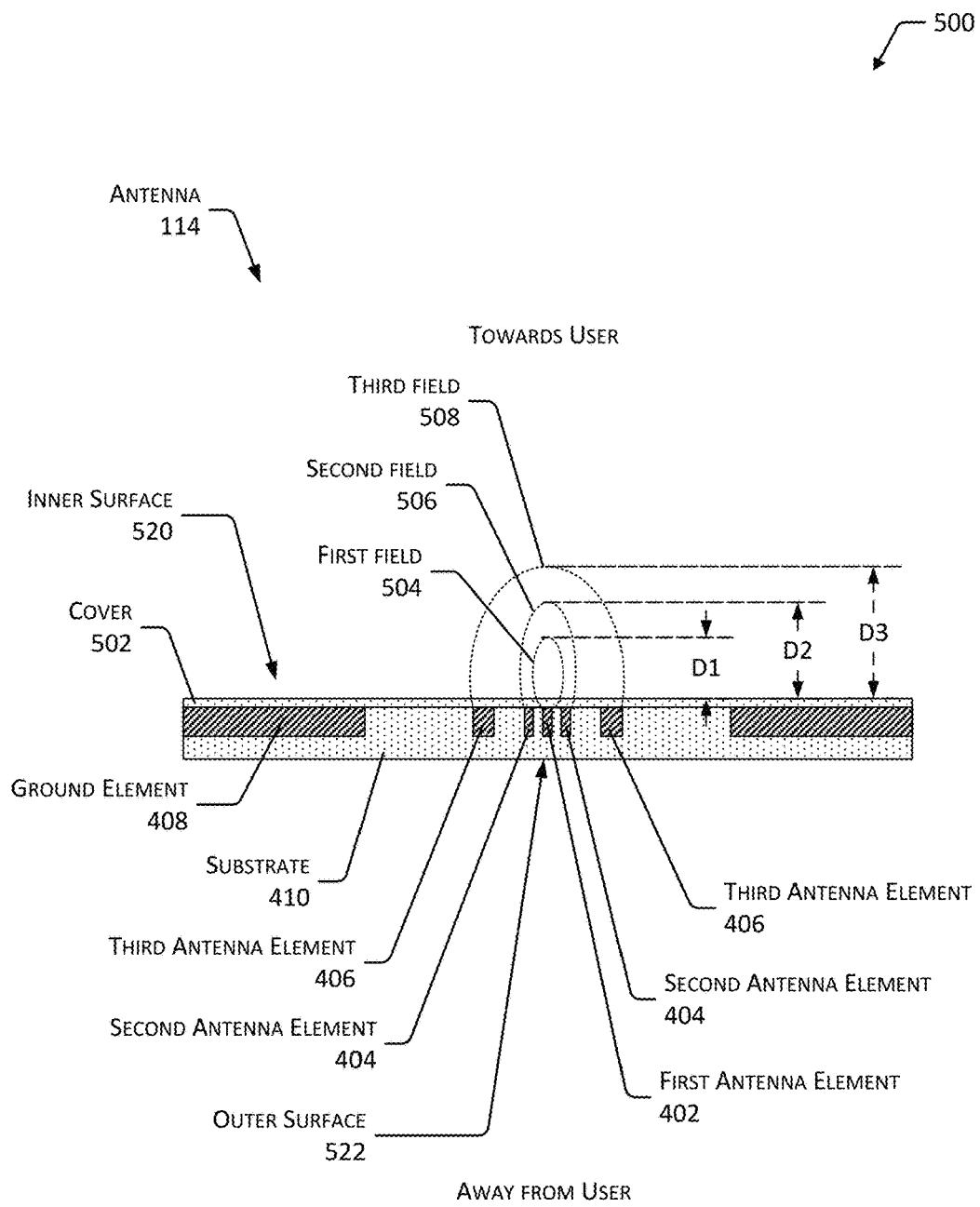
FIG. 5 illustrates a cross section of the antenna as shown in FIG. 4, according to one implementation.

FIG. 5 illustrates a cross section 500 of the antenna 114 as shown in FIG. 4, along line A-A, according to one implementation. As described with regard to FIG. 4, the antenna 114 comprises the first antenna element 402, the second antenna element 404, the third antenna element 406, and the ground element 408 that are supported by the substrate 410. In some implementations the system may include a ground plane or shield that is located behind the substrate 410 (not shown here), on a side opposite where the user 102 will be during use. For example, the ground plane may comprise a sheet of electrically conductive material.

Also depicted, by way of illustration and not as a limitation, are corresponding electrical fields that would extend from the combination of various sets of antenna elements, as switched by the antenna switching circuitry 120 during operation. A first field 504 corresponding to use of the first antenna element 402 is shown that extends a first distance D1 from the antenna 114. A second field 506 corresponding to use of the first antenna element 402 and the second antenna element 404 is shown that extends a second distance D2 from the antenna 114. The second distance D2 is greater than the first distance D1. A third field 508 corresponding to use of the first antenna element 402, the second antenna element 404, and the third antenna element 406 is shown that extends a third distance D3 from the antenna 114. The third distance D3 is greater than the second distance D2. By selecting different sets of antenna elements to use, different distances may be selected, allowing for measurement at different depths within the user 102.

The antenna elements may be located in a common plane, which may be designated as an antenna element layer. In other implementations one or more of the antenna elements may be positioned at different heights or have different thicknesses with respect to the substrate 410.

In the implementation depicted here, an uppermost surface of the antenna elements is flush or even with the substrate 410. This provides a flat or planar surface that is level in cross section across the first antenna element 402, the second antenna element 404, the third antenna element 406, and the ground element 408. In one implementation, this arrangement may be provided by the substrate 410 extending upward, as shown here. In another implementation a filler material may be used. In yet another implementation, the substrate 410 may be etched, milled, or formed to provide recesses within which the antenna elements may be placed to provide the desired cross section. By providing this flat cross section, longevity of the device may be improved, user comfort may be improved, and so forth. For example, the flat cross section precludes protrusions or edges that could wear during relative motion between the user 102 and the antenna 114.

In some implementations a cover 502 may be used that is adjacent to the antenna elements and is between the antenna elements and the user 102. The cover 502 may comprise a non-conductive material. For example, the cover 502 may comprise plastic, glass, or another material that is transparent to the signal(s) 108. In some implementations the cover 502 may be omitted. In these implementations, the antenna elements may come into direct contact with the skin of the user 102. The antenna elements may comprise a biocompatible material such as gold, silver, rhodium, and so forth. In addition to being used to emit and acquire the signal 108, in implementations where the antenna elements are in contact with the user 102, they may be used to acquire other information. For example, galvanic skin conductivity may be measured using two or more antenna elements, cardiac electrical signals may be acquired using one or more of the antenna elements, and so forth.

During wear, the support structure 110 maintains an inner surface 520 of the antenna 114 proximate to a portion of the user 102 while the wearable device 104 is being worn. An outer surface 522 of the antenna 114 is opposite, away from the user 102.

Figure 6:
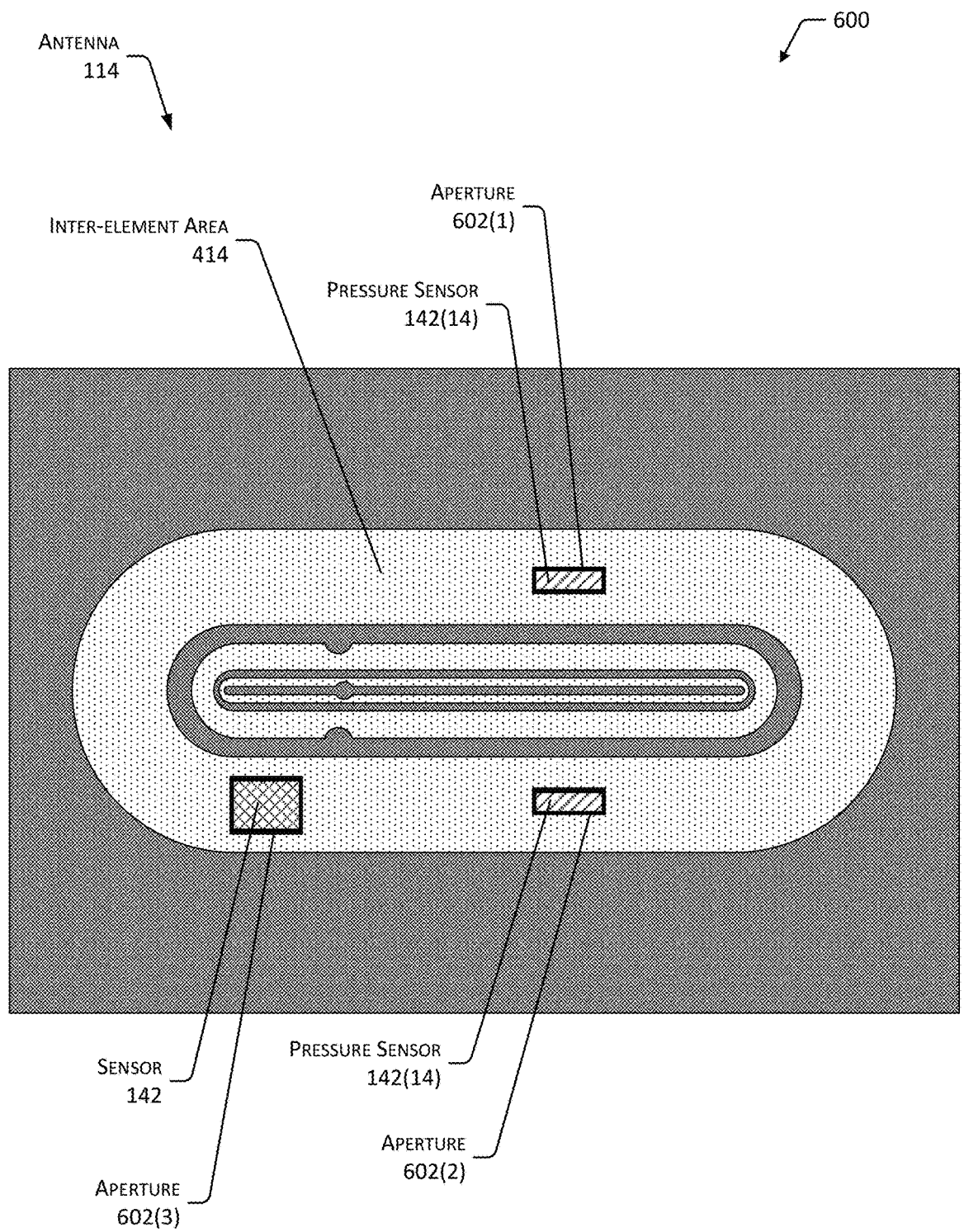
FIG. 6 illustrates some implementations of antenna elements in the antenna with apertures for other sensors, according to one implementation.

FIG. 6 illustrates at 600 some implementations of antenna elements in the antenna 114 with apertures for other sensors 142, according to one implementation. One or more apertures 602 or sensors 142 may be located within the inter-element area 414 of the antenna 114. The aperture 602 may provide a window or opening in the substrate 410 to facilitate operation of the wearable device 104. For example, the aperture 602 may provide a window through which an optical sensor such as a light emitting diode (LED) or a camera 142(7) is able to operate and acquire data about the user 102. In another example, the aperture 602 may be used by another sensor 142, such as a capacitive sensor, pressure sensor 142(14), and so forth. Some devices may be mounted to the substrate 410 or may be located between the antenna 114 and the user 102 during operation. For example, an LED may be affixed to the substrate 410 and when operated may illuminate a portion of the user 102 that is proximate to the inner surface of the wearable device 104.

In some implementations, sensors may operate through the substrate 410. For example, if the substrate 410 is flexible a pressure sensor 142(14) may operate through the substrate 410. In another example the substrate 410 may be transmissive to a signal being detected, such as a particular frequency of light.

Figure 7:
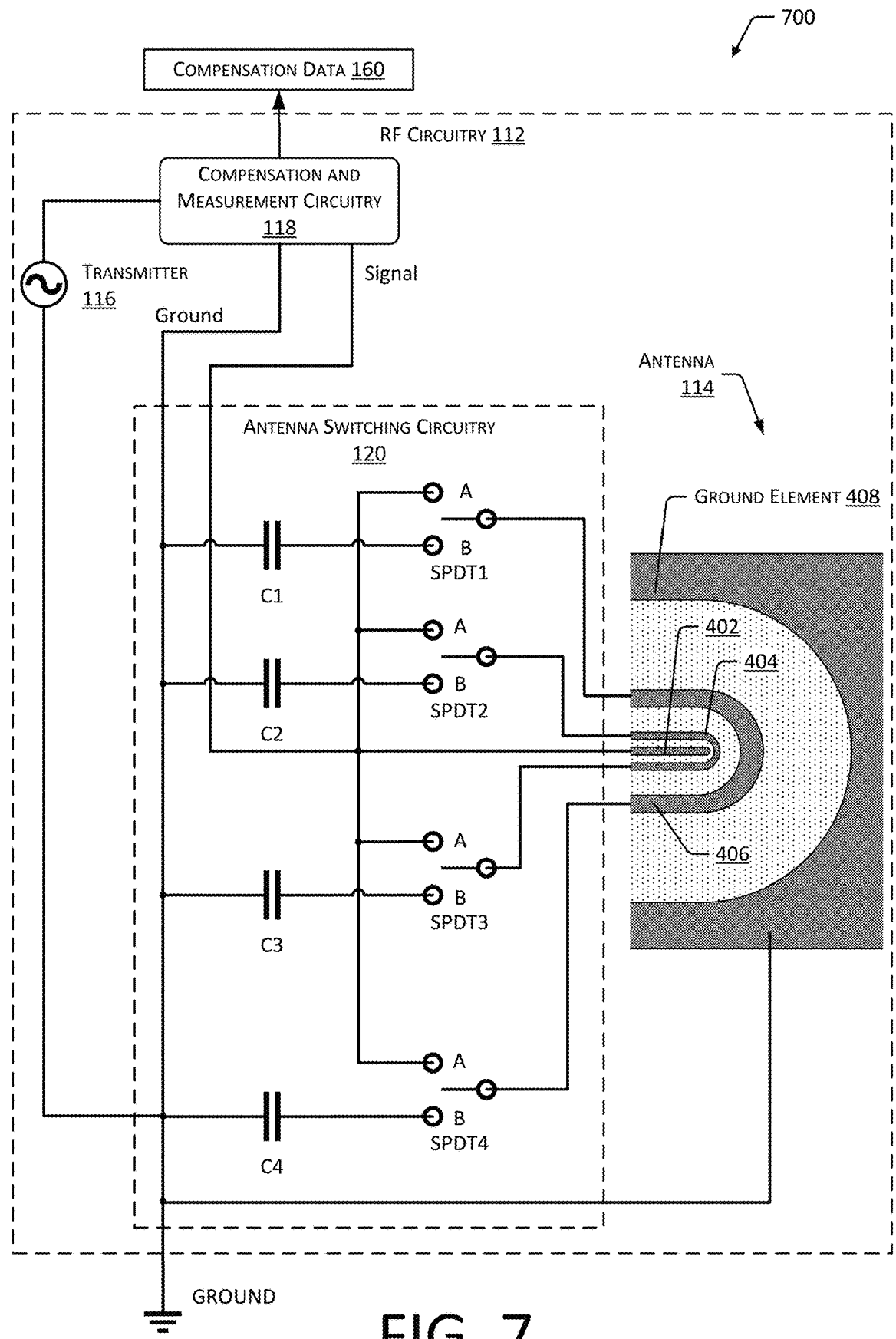
FIG. 7 is a circuit diagram of RF circuitry including antenna switching circuitry to select particular sets of antenna elements during operation, according to one implementation.

FIG. 7 is a circuit diagram 700 of the RF circuitry 112 including the antenna switching circuitry 120 to select particular sets of antenna elements of the antenna 114 during operation, according to one implementation. The antenna switching circuitry 120 allows various combinations of the first antenna element 402 to be connected to one or more of the second antenna element 404 or the third antenna element 406. In this illustration, the antenna switching circuitry 120 comprises four pairs of capacitors C1, C2, C3, and C4 and four single position double throw (SPDT) switches SPDT1, SPDT 2, SPDT3, and SPDT 4, or equivalent circuitry. Each SPDT has a first input terminal ("A") and a second input terminal ("B") and a single output terminal. In the implementation shown here, the first input terminal of each SPDT is connected to the output of the transmitter 116. The second input terminal of each SPDT is connected to a first terminal of a capacitor. A second terminal of each of the capacitors is connected to ground.

In some implementations, the antenna switching circuitry 120 may be operated according to the following truth table:

TABLE 1

|  | SPDT1 | SPDT2 | SPDT3 | SPDT4 |
| --- | --- | --- | --- | --- |
| Long Mode | A | A | A | A |
| Medium Mode | B | A | A | B |
| Short Mode | B | B | B | B |

The transmitter 116 has a first terminal and a second terminal. The first terminal provides signal output and is connected to the first antenna element 402. The second terminal is connected to a ground.

The antenna switching circuitry 120 comprises a third terminal connected to the first terminal and the first antenna element 402. A fourth terminal is connected to the second terminal, and is thus connected to ground.

A fifth terminal is connected to a first portion of the second antenna element 404. A sixth terminal is connected to a second portion of the second antenna element 404. A seventh terminal is connected to a first portion of the third antenna element 406. An eighth terminal is connected to a second portion of the third antenna element 406.

During operation, the antenna switching circuitry 120 may be directed to selectively connect one or more of the antenna elements to the output of the transmitter 116. For example, at a first time, the antenna switching circuitry 120 may operate to connect the third terminal to the fifth terminal, the sixth terminal, the seventh terminal, and the eighth terminal. Continuing the example, at a second time, the antenna switching circuitry 120 may operate to connect the third terminal to the fifth terminal, and the sixth terminal. At the second time the fourth terminal is also connected to the seventh terminal and the eighth terminal. Continuing the example, at a third time, the switching circuitry may operate to connect the fourth terminal to the fifth terminal, the sixth terminal, the seventh terminal, and the eighth terminal.

Also shown is compensation and measurement circuitry 118. The compensation and measurement circuitry 118 is configured to determine the compensation data 160 and also determine one or more operating values 128 associated with operation of the transmitter 116 while connected to one or more of the antenna elements. For example, the compensation and measurement circuitry 118 may be configured to determine the impedance presented by the antenna 114 at a particular frequency. The compensation and measurement circuitry 118 is discussed in more detail with regard to FIG. 9.

Figure 8:
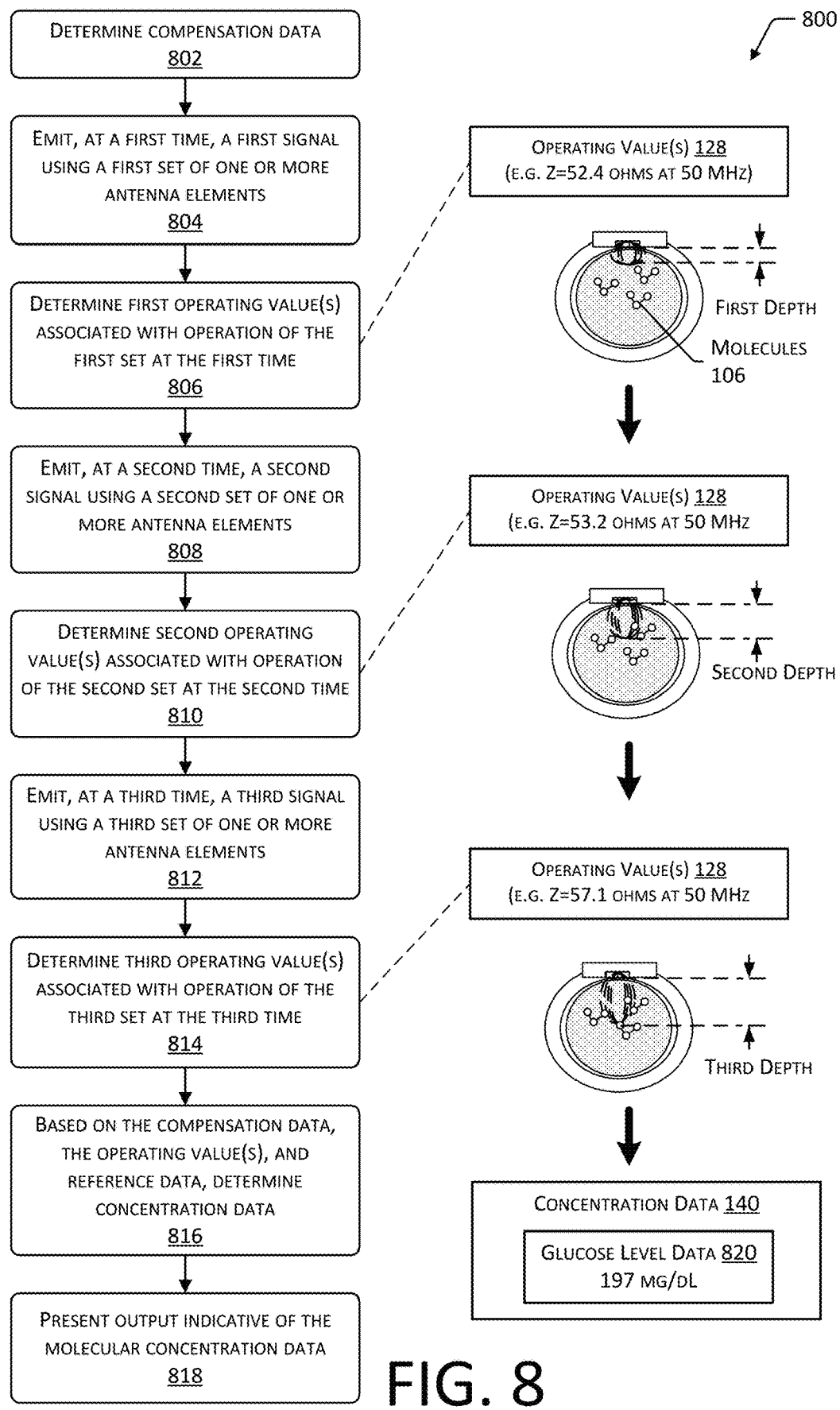
FIG. 8 illustrates a flow diagram of a process of using radio frequency signals emitted by the antenna to determine molecular concentration data, according to one implementation.

FIG. 8 illustrates a flow diagram 800 of a process of using radio frequency signals 108 emitted by the antenna 114 to determine molecular concentration data 140, according to one implementation. The process may be implemented at least in part by the wearable device 104.

At 802, compensation data 160 is determined. For example, the compensation and measurement circuitry 118 may be used to acquire a set of voltage values while particular known reference loads are connected to the output of the transmitter 116. The set of voltage values may then be used to determine the compensation data 160 indicative of the impedance of at least a portion of the RF circuitry 112. Determination of the compensation data 160 is discussed in more detail with regard to FIG. 10.

At 804, a first signal 108 is emitted at a first time using a first set of one or more antenna elements. For example, the antenna switching circuitry 120 may implement the "short mode" in which the first antenna element 402 is connected to the output of the transmitter 116 while the remaining antenna elements are connected to ground.

At 806, a first operating value 128 is determined that is associated with operation of the first set at the first time. For example, a first impedance presented by the first antenna element 402 to the transmitter 116 may be determined by the compensation and measurement circuitry 118.

At 808, a second signal 108 is emitted at a second time using a second set of one or more antenna elements. For example, the antenna switching circuitry 120 may implement the "medium mode" in which the first antenna element 402 and the second antenna element 404 are both connected to the output of the transmitter 116 while the remaining third antenna element 406 is connected to ground.

At 810, a second operating value 128 is determined that is associated with operation of the second set at the second time. For example, the second impedance presented by the combination of the first antenna element 402 and the second antenna element 404 to the transmitter 116 may be determined by the compensation and measurement circuitry 118.

At 812, a third signal 108 is emitted at a third time using a third set of one or more antenna elements. For example, the antenna switching circuitry 120 may implement the "long mode" in which the first antenna element 402, the second antenna element 404, and the third antenna element 406 are all connected to the output of the transmitter 116.

At 814, a third operating value 128 is determined that is associated with operation of the third set at the third time. For example, the third impedance presented by the combination of the first antenna element 402, the second antenna element 404, and the third antenna element 406 to the transmitter 116 may be determined by the compensation and measurement circuitry 118.

At 816, concentration data 140 is determined based on the compensation data 16 and operating values 128. For example, the compensation data 160 and the operating values 128 may be used to determine a measured impedance value. The measured impedance value and the reference data 138 may be used to determine the molecular concentration data 140. Continuing the example, the concentration data 140 may include glucose level data 820. In another example the operating value(s) 128 may be provided as input to a trained machine learning system which then provides as output the concentration data 140.

At 818 output indicative of the molecular concentration data 140 is presented. In one implementation, the user interface module 144 may generate output data 146 that is used by the one or more output devices 148 to present output to the user 102. For example, a graphical indication may be provided using a display device 148(3) of the other device 150.

While the system and techniques described herein are used with respect to measure humans, it is understood that these techniques may be used to monitor other types of animals. In some implementations, the systems and techniques may be used to characterize other objects. For example, the system may be used to determine a sugar concentration in a fruit, water concentration in a mixture, and so forth.

Figure 9:
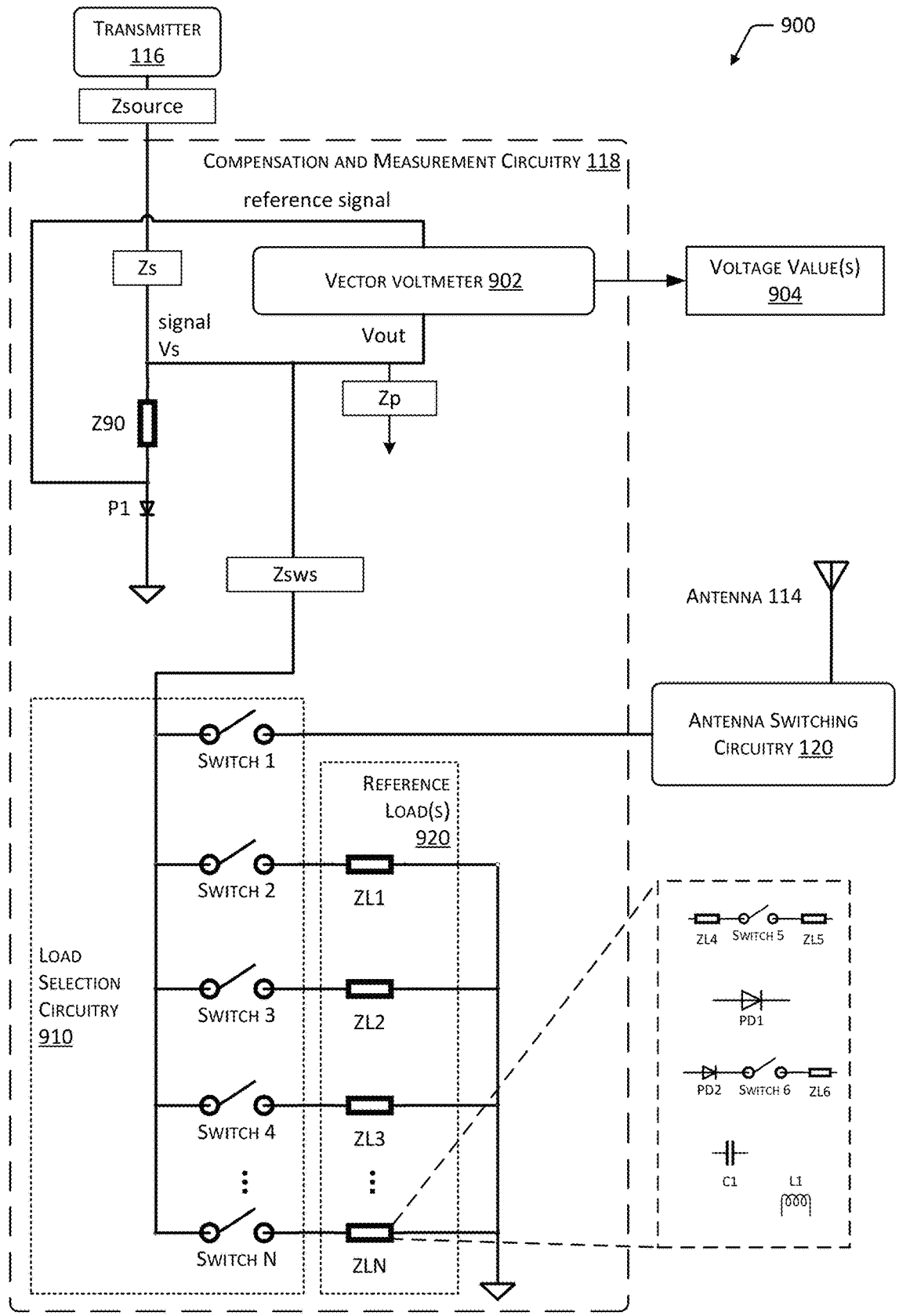
FIG. 9 is a circuit diagram of compensation and measurement circuitry that includes references loads, according to one implementation.

FIG. 9 is a circuit diagram 900 of the compensation and measurement circuitry 118, according to one implementation. The compensation and measurement circuitry 118 may comprise a vector voltmeter 902, load selection circuitry 910, and one or more reference loads 920.

During operation, the transmitter 116 outputs the signal 108 to a first terminal. The signal 108 has a voltage Vs. The impedance presented by the transmitter 116 is Zsource. A resistor Z90 has a second terminal connected to the first terminal, and a third terminal connected to ground. In some implementations a resistor or a PIN diode P1 may be present between the third terminal and the ground. The impedance produced by the resistor Z90 or PIN diode P1 may be used to control the amplitude of the signal 108. Stray series impedances, such as from printed circuit board (PCB) traces are shown as Zs.

The third terminal may also be connected to a fourth terminal of a vector voltmeter 902, providing an amplitude and phase reference to the vector voltmeter 902. The vector voltmeter 902 has a fifth terminal that is connected to a sixth terminal, providing a portion of the signal 108 Vout, to the vector voltmeter 902 for measurement. The sixth terminal is connected to the first terminal. During operation, the vector voltmeter 902 provides voltage values 904 as output. Stray parallel impedances associated with the vector voltmeter 902 and PCB traces are shown as Zp.

A seventh terminal is an input to load selection circuitry 910. The load selection circuitry 910 allows the signal 108 to be directed to one or more components of the device. For example, the load selection circuitry 910 may comprise switches, filters, and so forth. The seventh terminal is connected to the sixth terminal. Stray series impedance Zsws may include the impedance from PCB traces, series impedance from the switches in the load selection circuitry 910, and so forth. In the implementation shown here, the load selection circuitry 910 comprises a plurality of switching devices, each switching device having an input terminal and an output terminal. The input terminal for each switch device is connected to the seventh terminal, while the output terminal is connected to either the antenna 114 or a reference load 920.

The reference load 920 provides one or more known or controllable load elements that provide particular impedances. The reference load 920 may comprise one or more impedance devices. Each impedance device may comprise one or more components such as one or more fixed value resistors, one or more variable resistors, PIN diodes, capacitors, inductors, or combinations thereof. These components provide a specified impedance at the frequencies associated with the signal 108. For example, a PIN diode may be controlled to provide a particular impedance at a specified time during testing. The components that comprise the reference load(s) 920 may be high tolerance components. For example, the resistors in the reference load 920 may have a manufacturing tolerance of ±1%.

In the implementation depicted here, a first switch "switch 1" has a first input terminal connected to the seventh terminal, and a first output terminal connected to the antenna switching circuitry 120. During use to acquire measurements about the user 104, this switch is closed, allowing the signal 108 to reach the antenna 114. During operation of the compensation and measurement circuitry 118 to determine the compensation data 160, the first switch is open (preventing the signal 108 from reaching the antenna 114) and the signal 108 is dissipated by one or more of the components in the reference load(s) 920.

The second switch "switch 2" has a second input terminal connected to the seventh terminal, and a second output terminal connected to a first terminal of a first impedance device, such as resistor ZL1. The first impedance device, such as resistor ZL1, has a first impedance value that is known. A second terminal of the first resistor ZL1 is connected to ground.

The third switch "switch 3" has a third input terminal connected to the seventh terminal, and a third output terminal connected to a first terminal of a second impedance device, such as resistor ZL2. A second terminal of the second resistor ZL2 is connected to ground. The second resistor ZL2 has a second impedance value that is known.

The fourth switch "switch 4" has a fourth input terminal connected to the seventh terminal, and a fourth output terminal connected to a first terminal of a third impedance device, such as resistor ZL3. A second terminal of the third resistor ZL3 is connected to ground. The third resistor ZL3 has a third impedance value that is known.

The values of the impedances provided by the reference load 920 may be chosen to be close to the expected value of the unknown impedances to be measured. For example, if the unknown magnitude of the impedance to be measured is expected to be in the 50 to 200 ohm range, the reference loads 920 may comprise resistors with values of 50, 100, and 200 ohms.

In other implementations, the load selection circuitry 910 may include additional switches "switch N" and the associated reference loads 920 "ZLN" may be present. Other configurations of the components associated with the reference loads 920 may also be used. For example, reference loads 920 "ZLN" may include a fourth resistor "ZL4" connected in series, via a fifth switch "Switch 5", to a fifth resistor "ZL5". Operation of the fifth switch "Switch 5" may be used to include or exclude the fifth resistor "ZL5" from use, changing the impedance presented. In another implementation, switches 2 through n may be omitted and a PIN diode "PD1" may be controlled to provide a desired impedance at different times while determining the compensation data 160. In another implementation, reference loads 920 "ZLN" may include a PIN diode "PD2" connected in series via a sixth switch "Switch 6" to a sixth resistor "ZL6." In yet another implementation, reference loads 920 "ZLN" may include a capacitor "C1", an inductor "L1", or any combination thereof.

During operation to determine the compensation data 160, the load selection circuitry 910 connects one or more of the reference loads 920 to the output of the transmitter 116. While connected, the transmitter 116 provides the signal 108 and the vector voltmeter 902 generates a voltage value 904. As different reference loads 920 or combinations thereof are connected to the transmitter 116, additional voltage values 904 are acquired, forming a set of voltage values 904.

In other implementations, other circuitry may be used instead of a vector voltmeter 902. For example, other circuitry may include one or more of a voltmeter, a phase comparator, a vector network analyzer, and so forth.

Instead of, or in addition to switching devices, the load selection circuitry 910 may use other techniques to direct the signal 108 to the antenna 114 or particular reference loads 920. In one implementation, each of the outputs of the load selection circuitry 910 may be associated with different filter devices. Each filter device may pass a different frequency. By operating the transmitter 116 at different frequencies, the resulting signals 108 may be directed to a particular output of the load selection circuitry 910. For example, during operation to determine concentration data 140, the transmitter 116 may generate a signal 108 at 5.8 GHz. A first filter element operating as a narrow band pass filter may pass the 5.8 GHz signal 108 to the antenna 114, while other filter elements prevent the signal 108 from reaching the reference loads 920. Continuing the example, during determination of the compensation data 160, the transmitter 118 may generate a signal 108 at 5.73 GHz. The first filter element prevents the signal 108 from reaching the antenna 114, while a second filter element operating as a narrow band pass filter passes the 5.73 GHz signal to the first impedance device of the reference load 920, such as ZL1.

Figure 10:
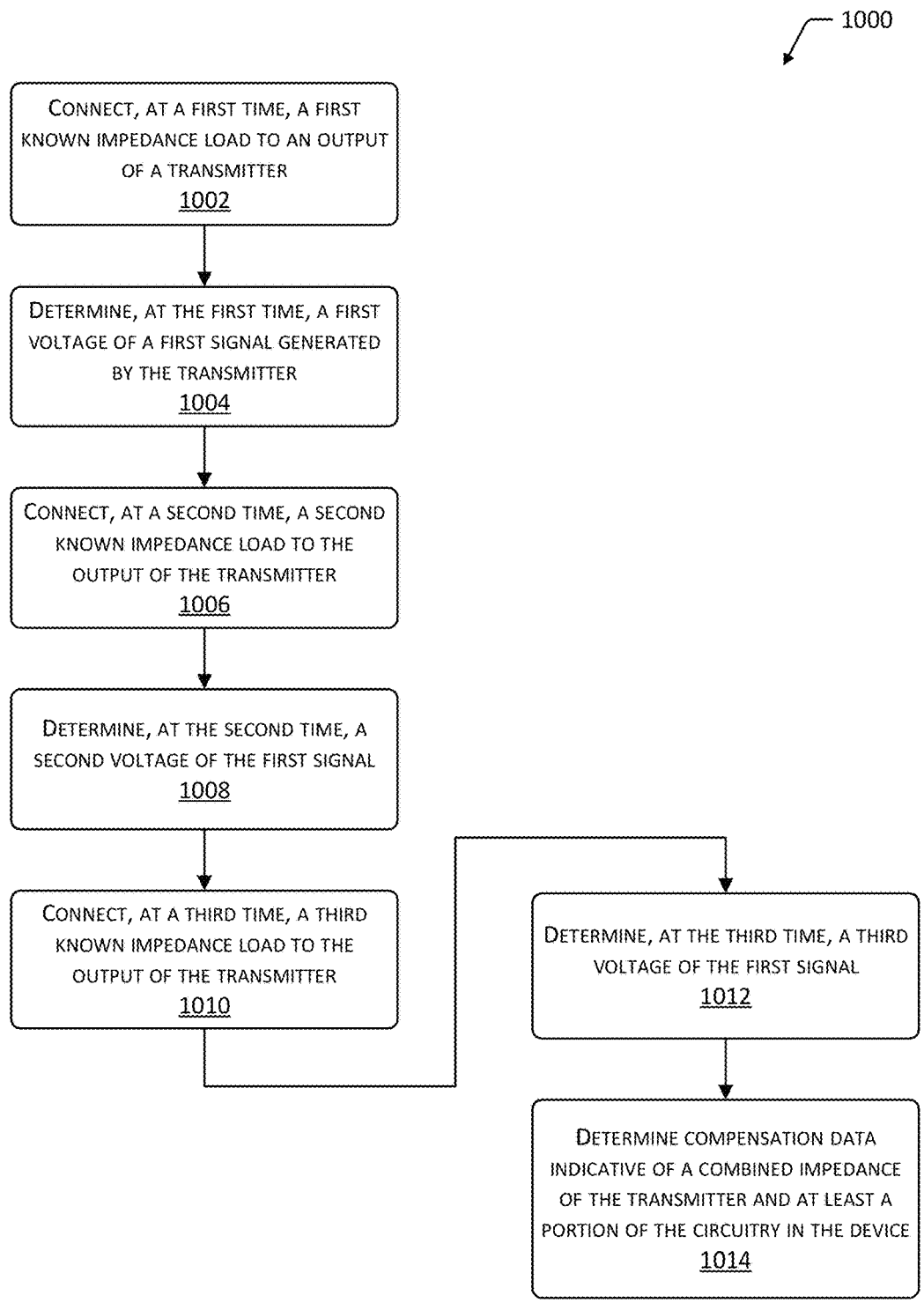
FIG. 10 illustrates a flow diagram of a process of determining compensation data using reference loads, according to one implementation.

FIG. 10 illustrates a flow diagram 1000 of a process of determining compensation data 160 using reference loads 920, according to one implementation. The process connects different known reference loads 920 to the transmitter 116 generating the signal 108 at different times, and determines the voltage values 904 indicative of the resulting voltages associated with those known reference loads 920. The process may be implemented at least in part by the wearable device 104.

At 1002, a first known impedance load is connected at a first time to an output of the transmitter 116. For example, the load selection circuitry 910 may open the first switch "switch 1", close the second switch "switch 2" to connect the first reference load 920(1) comprising the first resistor ZL1 to the transmitter 116 output.

At 1004 a first voltage value 904(1) of a first signal 108 generated by the transmitter 116 is determined at or after the first time. For example, the vector voltmeter 902 may measure Vout and generate a corresponding first voltage value 904(1) indicative of a first voltage.

At 1006, a second known impedance load is connected at a second time to an output of the transmitter 116. For example, the load selection circuitry 910 may open the first switch "switch 1", open the second switch "switch 2", and close the third switch "switch 3" to connect the second reference load 920(2) comprising the second resistor ZL2 to the transmitter 116 output.

At 1008 a second voltage value 904(2) of the first signal 108 generated by the transmitter 116 is determined at or after the second time. For example, the vector voltmeter 902 may measure Vout and generate a corresponding second voltage value 904(2) indicative of a second voltage.

At 1010, a third known impedance load is connected at a third time to output of the transmitter 116. For example, the load selection circuitry 910 may open the first switch "switch 1", open the second switch "switch 2", open the third switch "switch 3", and close the fourth switch "switch 4" to connect the third reference load 920(3) comprising the third resistor ZL3 to the transmitter 116 output.

At 1012 a third voltage value 904(3) of the first signal 108 generated by the transmitter 116 is determined at or after the third time. For example, the vector voltmeter 902 may measure Vout and generate a corresponding third voltage value 904(3) indicative of a third voltage.

At 1014 compensation data 160 is determined based at least in part on a set of voltage values comprising the first voltage value 904(1), the second voltage value 904(2), the third voltage value 904(3) that may be used along with the values of the associated reference loads 920 to determine unknown impedance Z of at least a portion of the RF circuitry 112.

The compensation data 160 may be expressed as the unknown impedance Z. This unknown impedance Z may be representative of the impedances presented by the circuitry including a portion of the transmitter 116 and at least a portion of the load selection circuitry 910. For example, the unknown impedance Z may result from Zs, Zp, Zsws, and so forth.

In one implementation, the unknown impedance Z may be determined using the following equations, where:

Voutm1 is the first voltage value 904(1) measured while using the first reference load 920(1), Voutm2 is the second voltage value 904(2) measured while using the second reference load 920(2), Voutm3 is the third voltage value 904(3) measured while using the third reference load 920(3), ZL1 is the first resistance value of the first resistor in the first reference load 920(1), ZL2 is the second resistance value of the second resistor in the second reference load 920(2), and ZL3 is the third resistance value of the third resistor in the third reference load 920(3).

$$Zs = \frac{(Voutm1 - Voutm2)(ZL2 - ZL3)(ZL1 - ZL3)}{(Voutm2 - Voutm3)(Voutm1 - Voutm3)(ZL1 - ZL2)} \\ \overline{(((zL1 - ZL2)Voutm2 - Voutm3(ZL1 - ZL3))Voutm1 + Voutm2Voutm3(ZL2 - ZL3))^2}$$ (Equation 1)

$$Zp = \frac{Zna}{Zda}$$ (Equation 2)

where $$Zna = (Voutm1 - Voutm2)(ZL2 - ZL3)(ZL1 - ZL3)$$ (Equation 2a)

$$Zda = \frac{(Voutm2 - Voutm3)(Voutm1 - Voutm3)(ZL1 - ZL2)}{(((ZL1 - ZL2)Voutm2 + (-ZL1 + ZL3)Voutm3 + ZL2 - ZL3)} \\ Voutm1 + ((ZL2 - ZL3)Voutm3 - ZL1 + ZL3) \\ Voutm2 + Voutm3(ZL1 - ZL2)) \\ (((ZL1 - ZL2)Voutm2 - Voutm3(ZL1 - ZL3))Voutm1 + \\ Voutm2Voutm3(VL2 - ZL3))$$ (Equation 2b)

$$Zsws = \frac{Znb}{Zdb}$$ (Equation 3)

where $$Znb = (-ZL3(ZL1-ZL2)Voutm2 + ZL2Voutm3(ZL1-ZL3))Voutm1 - ZL1Voutm2Voutm3(ZL2-ZL3)$$ (Equation 3a)

$$Zdb = ((ZL1-ZL2)Voutm2 - Voutm3(ZL1-ZL3)) \\ Voutm1 + Voutm2Voutm3(ZL2-ZL3)$$ (Equation 3b)

As shown in Equation 4, the value of Vs may be solved for a given measured value of Vout, such as a voltage value 904 and a known value for Z in Equation 4, for example when Z=ZL2 and Vout=Voutm2.

$$Vs = \frac{Vout(Z + Zsws + Zp)\left(\frac{(Z + Zsws)Zp}{Z + Zsws + Zp} + Zs\right)}{(Z + Zsws)Zp}$$ (Equation 4)

Equation 5 may be used to determine the unknown impedance Z of at least a portion of the circuitry that is represented by the compensation data 160, where Vs is equal to the value Vs obtained from Equation 4.

$$Z = \frac{VoutZpZs + VoutZPZsws + VoutZsZsws - ZpVsZsws}{VoutZp + ZsVout - ZpVs}$$ (Equation 5)

While the process describes determining voltage values 904 for three known reference loads, in other implementations the process may use fewer reference loads or more known reference loads.

The process to determine the compensation data 160 may be performed responsive to one or more inputs or triggers.

These inputs may be indicative of internal operation of the wearable device 104, responsive to data from the clock 306 or one or more sensors 142, and so forth.

Changes in supply voltage to the compensation and measurement circuitry 118 may affect the resulting voltage values 904 that are then used to determine the impedance data 132. To mitigate these effects, compensation data 160 may be determined that compensates for this. In a first example, the compensation data 160 may be determined responsive to a change in voltage of power provided by the power supply 302 of the wearable device 104 from a first time to a second time, wherein the change exceeds a threshold value. In a second example, the compensation data 160 may be responsive to a change in charge state, such as the available battery charge dropping below a specified percentage.

The clock 306 may be used to trigger determination of compensation data 160 after some elapsed time. In a third example, an elapsed time since last determination of compensation data 160 that has exceeded a first threshold value may result in determination of compensation data 160. Continuing the example, the compensation data 160 may be determined every 600 seconds.

Environment changes may affect operation of the RF circuitry 112 or other circuitry within the device 104. For example, changes in temperature may affect internal impedances of the RF circuitry 112, may change the frequency of a local oscillator, and so forth. In a fourth example, a change in temperature data associated with the device 104 from a first time to a second time that exceeds a second threshold value may result in determination of compensation data 160. Continuing the example, if the temperature reported by a temperature sensor 142(6) indicates that the temperature has changed by more than 2 degrees Centigrade within the last ten minutes, the compensation data 160 may be determined.

In implementations where the device 104 is wearable, increased motion may be indicative of increased activity of the user 102. In a fifth example, motion data associated with the device 102 that exceeds a third threshold value may result in determination of compensation data 160. Continuing the example, if average overall acceleration as measured by the accelerometer(s) 142(10) exceeds 1 m/s^2/second, the device 104 may be deemed to be in motion, and the compensation data 160 may be determined.

Similarly, data from other sensors 142 may be used to trigger the determination of the compensation data 160. In a sixth example, pulse data indicative of a cardiac pulse rate that is associated with a user 104 of the device 104 that exceeds a fourth threshold value may result in determination of compensation data 160. Continuing the example, if the heart rate monitor 142(3) determines that the pulse exceeds a user's resting rate by more than 10%, the compensation data 160 may be determined.

Data determined by the compensation and measurement circuitry 118 may also be used to trigger the determination of the compensation data 160. A voltage value 904 reported by the vector voltmeter 902 during operation to determine impedance data 132 of the antenna 114 such as during measurement of the user 102, or during compensation data 160 determination, may result in triggering determination of the compensation data 160.

In a seventh example, a first voltage measured by the vector voltmeter 902 that is greater than a maximum threshold value may trigger determination of the compensation data 160. The maximum threshold value may be specified as a fixed value, percentage change compared to previous measurement, and so forth.

In an eighth example, the first voltage measured by the vector voltmeter 902 that is less than a minimum threshold value may trigger determination of the compensation data 160. The minimum threshold value may be specified as a fixed value, percentage change compared to previous measurement, and so forth.

Figure 11:
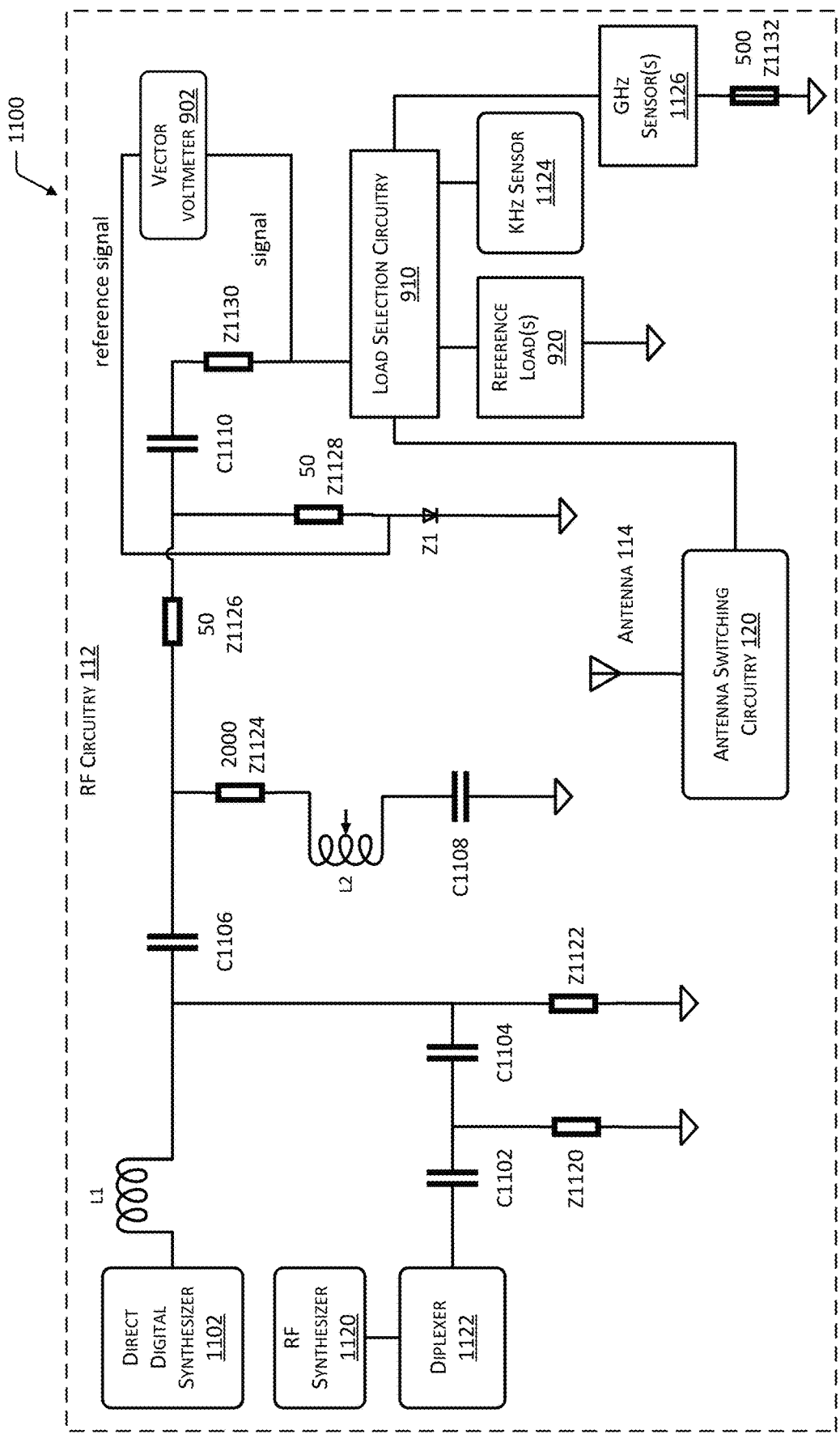
FIG. 11 is a block diagram of one implementation of the RF circuitry, according to one implementation.

FIG. 11 is a block diagram 1100 of one implementation of the RF circuitry 112. The RF circuitry 112 may comprise a direct digital synthesizer (DDS) 1102 to generate the signal 108 in the megahertz (MHz) frequency range. For example, the DDS 1102 may comprise an AD9913 CMOS direct digital synthesizer from Analog Devices, Inc. of Norwood, Massachusetts, United States of America. Output from the DDS 1102 may be provided to a first terminal of inductor L1. A second terminal of the inductor L2 is connected to a third terminal. A fourth terminal of capacitor C1106 is connected to the third terminal. A fifth terminal of the capacitor C1106 is connected to a sixth terminal. A seventh terminal of resistor Z1124 is connected to the sixth terminal. An eighth terminal of the resistor Z1124 is connected to a ninth terminal of inductor L2. A tenth terminal of the inductor L2 is connected to an eleventh terminal of capacitor C1108. A twelfth terminal of the capacitor C1108 is connected to ground.

The sixth terminal is also connected to a thirteenth terminal of resistor Z1126. A fourteenth terminal of resistor Z1126 is connected to a fifteenth terminal of capacitor C1110. A sixteenth terminal of the capacitor C1110 is connected to a seventeenth terminal of resistor Z1130. An eighteenth terminal of resistor Z1130 is connected to a nineteenth terminal of the load selection circuitry 910.

The fifteenth terminal is also connected to a twentieth terminal of resistor Z1128. A twenty-first terminal of the resistor Z1128 is connected to a twenty-second terminal. The twenty-second terminal is connected to a twenty-third terminal of PIN diode Z1. A twenty-fourth terminal of the PIN diode Z1 is connected to ground. The twenty-second terminal is also connected to an input to the vector voltmeter 902. This connection provides the reference signal to the vector voltmeter 902. In some implementations the vector voltmeter 902 may comprise a phase detector. For example, the vector voltmeter 902 may comprise a phase detector such as an AD8302 from Analog Devices, Inc. of Norwood, Massachusetts, United States of America. Output from the phase detector AD8302 may be provided to an analog-to-digital (ADC) converter such as an ADS124S06 from Texas Instruments, Inc. of Dallas, Texas, United States of America.

The load selection circuitry 910 is connected to the antenna switching circuitry 120, as described previously. The antenna switching circuitry 120 is connected to the antenna 114. The load selection circuitry 910 is also connected to the reference load(s) 920.

The load selection circuitry 910 may also be connected to a kilohertz (KHz) sensor 1124. The kilohertz sensor 1124 may use a signal 108 in the kilohertz range that is used to detect presence of the user 102.

The load selection circuitry 910 may also be connected to one or more gigahertz (GHz) sensors 1126. The GHz sensors 1126 may be connected, via one or more resistors, such as ZL1132, to ground.

The RF circuitry 112 may comprise an RF synthesizer 1120 to generate the signal 108 in the gigahertz (GHz) frequency range. For example, the RF synthesizer 1102 may comprise a SI4136-GM RF synthesizer from Silicon Labs, Inc. of Austin, Texas, United States of America. In some implementations, a plurality of signal outputs from the RF synthesizer 1120 may be combined by a diplexer 1122. The diplexer 1122 may comprise a DPX202690DT-4060A1 from TDK Corporation of America of Uniondale, New York, United States of America. Output from the diplexer 1122 is connected to a thirty-eighth terminal of capacitor C1102. A thirty-ninth terminal of capacitor C1102 is connected to a fortieth terminal. The fortieth terminal is connected to a forty-first terminal of resistor Z1120. A forty-second terminal of resistor Z1120 is connected to ground. The fortieth terminal is also connected to a forty-third terminal of capacitor C1104. A forty-fourth terminal of capacitor C1104 is connected to the third terminal. The forty-fourth terminal of capacitor C1104 is also connected to a forty-fifth terminal of resistor Z1122. A forty-sixth terminal of resistor Z1122 is connected to ground.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations.

Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A wearable device comprising:
    a support structure that retains the wearable device proximate to a user;
    an antenna mounted to the support structure:
    a transmitter connected to a first terminal;
    a vector voltmeter having a voltmeter input terminal connected to the first terminal;
    load selection circuitry comprising:
        a first switch having a first input terminal connected to the first terminal and a first output terminal connected to the antenna;
        a second switch having a second input terminal connected to the first terminal and a second output terminal connected to a first resistor having a first resistance value;
        a third switch having a third input terminal connected to the first terminal and a third output terminal connected to a second resistor having a second resistance value; and
        a fourth switch having a fourth input terminal connected to the first terminal and a fourth output terminal connected to a third resistor having a third resistance value;
    a memory, storing computer-executable instructions; and
    a hardware processor that executes the computer-executable instructions to:
        operate, at a first time, the second switch to connect the first terminal to the second output terminal;
        generate a first signal using the transmitter, wherein the first signal is dissipated at least in part by the first resistor;
        determine, using the vector voltmeter, a first voltage of the first signal at the first time;
        operate, at a second time, the third switch to connect the first terminal to the third output terminal;
        generate a second signal using the transmitter, wherein the second signal is dissipated at least in part by the second resistor;
        determine, using the vector voltmeter, a second voltage of the second signal at the second time;
        operate, at a third time, the fourth switch to connect the first terminal to the fourth output terminal;
        generate a third signal using the transmitter, wherein the third signal is dissipated at least in part by the third resistor;
        determine, using the vector voltmeter, a third voltage of the third signal at the third time; and
        determine compensation data indicative of combined impedance of the transmitter and at least a portion of circuitry of the wearable device based on the first voltage, the second voltage, the third voltage, the first resistance value, the second resistance value, and the third resistance value.

2. The wearable device of claim 1, wherein the hardware processor further executes the computer-executable instructions to:
    operate, at a fourth time, the first switch to connect the first terminal to the first output terminal;

generate a fourth signal using the transmitter, wherein the fourth signal is dissipated at least in part by the antenna;

determine, using the vector voltmeter, a fourth voltage of the fourth signal at the fourth time;

determine, based on the fourth voltage, a first impedance value;

determine, based on the compensation data and the first impedance value, a second impedance value; and determine, based at least in part on the second impedance value, a concentration value of a type of molecule within the user.

3. A device comprising:
an antenna having a first input terminal;
one or more radio frequency (RF) transmitters having a first output terminal;
a vector voltmeter having a second input terminal;
circuitry comprising:
  a third input terminal;
  a second output terminal connected to the first input terminal;
  one or more load elements; and
  one or more switching devices to selectively connect the third input terminal to one or more of the second output terminal or the one or more load elements;
  a first terminal connected to:
    the first output terminal,
    the second input terminal, and
    the third input terminal; and
one or more hardware processors to execute instructions to:
  operate the one or more RF transmitters and the circuitry to acquire a first set of voltage values using the vector voltmeter; and
  determine compensation data indicative of combined impedance presented by at least a portion of the device.

4. The device of claim 3, the one or more load elements comprising one or more of:
  a first fixed value impedance device,
  a second fixed value impedance device connected in series via a first switching device to a third fixed value impedance device,
  a first PIN diode, or
  a second PIN diode connected in series via a second switching device to a fourth fixed value impedance device.

5. The device of claim 3, the one or more load elements comprising a first impedance device, a second impedance device, and a third impedance device; and
  the one or more switching devices comprising:
    a first switch to connect the third input terminal to the first input terminal;
    a second switch to connect the third input terminal to the first impedance device having a first resistance value;
    a third switch to connect the third input terminal to the second impedance device having a second resistance value; and
    a fourth switch to connect the third input terminal to the third impedance device having a third resistance value.

6. The device of claim 5, wherein the one or more hardware processors execute instructions to:
  operate, at a first time, the second switch to connect the third input terminal to the first impedance device;

generate a first signal using the one or more RF transmitters, wherein the first signal is dissipated at least in part by the first impedance device;

determine, using the vector voltmeter, a first voltage of the first signal at the first time;

operate, at a second time, the third switch to connect the third input terminal to the second impedance device;

generate a second signal using the one or more RF transmitters, wherein the second signal is dissipated at least in part by the second impedance device;

determine, using the vector voltmeter, a second voltage of the second signal at the second time;

operate, at a third time, the fourth switch to connect the third input terminal to the third impedance device;

generate a third signal using the one or more RF transmitters, wherein the third signal is dissipated at least in part by the third impedance device;

determine, using the vector voltmeter, a third voltage of the third signal at the third time; and wherein the first set of voltage values comprises the first voltage, the second voltage, and the third voltage.

7. The device of claim 3, wherein the one or more hardware processors execute instructions to:
  determine the compensation data responsive to one or more of:
    a change in voltage of power provided by a power supply of the device from a first time to a second time, wherein the change exceeds a first threshold value,
    an elapsed time since last determination of compensation data has exceeded a second threshold value,
    a change in temperature data associated with the device from a third time to a fourth time exceeds a third threshold value,
    motion data associated with the device exceeds a fourth threshold value,
    pulse data associated with a user of the device exceeds a fifth threshold value,
    a first voltage measured by the vector voltmeter is greater than a sixth threshold value, or
    the first voltage measured by the vector voltmeter is less than a seventh threshold value.

8. The device of claim 3, wherein the one or more hardware processors execute instructions to:
  operate the one or more switching devices to connect the first input terminal to the first output terminal;
  generate a signal using the one or more RF transmitters, wherein the signal is dissipated at least in part by the antenna;
  determine, using the vector voltmeter, a first voltage of the signal;
  determine, based on the first voltage, a first impedance value;
  determine, based on the compensation data and the first impedance value, a second impedance value; and
  determine, based at least in part on the second impedance value, a concentration value of a type of molecule within a user.

9. The device of claim 3, wherein the compensation data is associated with the one or more RF transmitters operating within a first frequency range; and
  the one or more hardware processors to execute instructions to:
    operate the one or more RF transmitters within a second frequency range and the circuitry to acquire a second set of voltage values using the vector voltmeter; and determine second compensation data associated with the second frequency range.

10. The device of claim 3, wherein the antenna comprises:
a first antenna element,
a second antenna element, and
a third antenna element; and
the device further comprising antenna switching circuitry comprising:
the first input terminal,
the one or more switching devices to selectively connect the first input terminal to one or more of the first antenna element, the second antenna element, or the third antenna element; and
wherein the one or more hardware processors execute the instructions to:
operate the antenna switching circuitry.

11. A device comprising:
an antenna having a first input terminal;
one or more radio frequency (RF) transmitters having a first output terminal;
first circuitry having a second input terminal, wherein the first circuitry measures voltage;
second circuitry comprising:
a third input terminal;
a second output terminal connected to the first input terminal;
one or more load elements; and
third circuitry to selectively connect the third input terminal to one or more of the second output terminal or the one or more load elements;
a first terminal connected to:
the first output terminal,
the second input terminal, and
the third input terminal; and
one or more hardware processors to execute instructions to:
operate the one or more RF transmitters and the second circuitry to acquire a first set of voltage values using the first circuitry; and
determine first data indicative of combined impedance presented by at least a portion of the device.

12. The device of claim 11, wherein the first circuitry comprises a vector voltmeter.

13. The device of claim 11, the one or more load elements comprising one or more of:
a first fixed value resistor,
a first fixed value capacitor,
a first inductor,
a second fixed value resistor connected in series via a first switching device to a third fixed value resistor,
a first PIN diode, or
a second PIN diode connected in series via a second switching device to a fourth fixed value resistor.

14. The device of claim 11, the one or more load elements comprising:
a first impedance device having a first resistance value,
a second impedance device having a second resistance value, and
a third impedance device having a third resistance value; and
the third circuitry comprising:
a first switch to connect the third input terminal to the first input terminal;
a second switch to connect the third input terminal to the first impedance device;
a third switch to connect the third input terminal to the second impedance device; and
a fourth switch to connect the third input terminal to the third impedance device.

15. The device of claim 14, wherein the one or more hardware processors execute instructions to:
operate, at a first time, the second switch to connect the third input terminal to the first impedance device;
generate a first signal using the one or more RF transmitters, wherein the first signal is dissipated at least in part by the first impedance device;
determine, using the first circuitry, a first voltage of the first signal at the first time;
operate, at a second time, the third switch to connect the third input terminal to the second impedance device;
generate a second signal using the one or more RF transmitters, wherein the second signal is dissipated at least in part by the second impedance device;
determine, using the first circuitry, a second voltage of the second signal at the second time;
operate, at a third time, the fourth switch to connect the third input terminal to the third impedance device;
generate a third signal using the one or more RF transmitters, wherein the third signal is dissipated at least in part by the third impedance device;
determine, using the first circuitry, a third voltage of the third signal at the third time; and
wherein the first set of voltage values comprises the first voltage, the second voltage, and the third voltage.

16. The device of claim 11, wherein the one or more hardware processors execute instructions to:
determine the first data responsive to one or more of:
a change in voltage of power provided by a power supply of the device from a first time to a second time, wherein the change exceeds a first threshold value,
an elapsed time since last determination of the first data has exceeded a second threshold value,
a change in temperature data associated with the device from a third time to a fourth time exceeds a third threshold value,
motion data associated with the device exceeds a fourth threshold value,
pulse data associated with a user of the device exceeds a fifth threshold value,
a first voltage measured by the first circuitry is greater than a sixth threshold value, or
the first voltage measured by the first circuitry is less than a seventh threshold value.

17. The device of claim 11, wherein the one or more hardware processors execute instructions to:
operate the third circuitry to connect the first input terminal to the first output terminal;
generate a signal using the one or more RF transmitters, wherein the signal is dissipated at least in part by the antenna;
determine, using the first circuitry, a first voltage of the signal;
determine, based on the first voltage, a first impedance value;
determine, based on the first data and the first impedance value, a second impedance value; and
determine, based at least in part on the second impedance value, a concentration value of a type of molecule within a user.

18. The device of claim 11, wherein the first data is associated with the one or more RF transmitters operating within a first frequency range; and the one or more hardware processors execute instructions to:
  operate the one or more RF transmitters within a second frequency range and the second circuitry to acquire a second set of voltage values using the first circuitry; and
  determine second data associated with the second frequency range.

19. The device of claim 11, wherein the antenna comprises:
  a first antenna element,
  a second antenna element, and
  a third antenna element; and
  the device further comprising antenna switching circuitry comprising:
  the first input terminal,
  the third circuitry to selectively connect the first input terminal to one or more of the first antenna element, the second antenna element, or the third antenna element; and
  wherein the one or more hardware processors execute the instructions to:
  operate the antenna switching circuitry.

20. The device of claim 11, further comprising:
  a PIN diode having:
    a second terminal connected to the first terminal, and
    a third terminal connected to ground.

* * * * *